(12) United States Patent
Sibi et al.

(10) Patent No.: US 8,034,974 B2
(45) Date of Patent: Oct. 11, 2011

(54) BETA-AMINO ACIDS AND METHODS INTERMEDIATES FOR MAKING SAME

(75) Inventors: Mukund P. Sibi, Fargo, ND (US); Craig P. Jasperse, Moorhead, MN (US); Prabagaran Narayanasamy, Fargo, ND (US); Sandeep R. Ghorpade, Mumbai (IN)

(73) Assignee: NDSU Research Foundation, Fargo, ND (US)

( * ) Notice: Subject to any disclaimer, the term of this patent is extended or adjusted under 35 U.S.C. 154(b) by 870 days.

(21) Appl. No.: 10/895,647

(22) Filed: Jul. 21, 2004

(65) Prior Publication Data

US 2011/0218342 A1    Sep. 8, 2011

Related U.S. Application Data

(60) Provisional application No. 60/488,947, filed on Jul. 21, 2003.

(51) Int. Cl.
*C07C 229/08* (2006.01)
*C07C 229/10* (2006.01)
(52) U.S. Cl. .................. 562/553; 562/571; 562/576
(58) Field of Classification Search .................. None
See application file for complete search history.

(56) References Cited

U.S. PATENT DOCUMENTS

| 6,080,857 | A | 6/2000 | Sibi et al. |
| 6,191,283 | B1 | 2/2001 | Sibi et al. |

OTHER PUBLICATIONS

Lee et al. Journal of Organic Chemistry, 2003, 68, 1575.*
Davies et al., "Asymmetric Syntheses of beta-Phenylalanine, alpha-Methyl-beta-Phenylalanines and Derivatives," *J. Chem. Soc. Chem. Comm.*, (14):1153-1155 (1993).
Ishikawa et al., Asymmetric Synthesis of Substituted Isoxazolidinone form alpha,beta-Unsaturated Esters and Hydroxylamines by Means of Double Stereodifferentiation, *Synlett.*, (11):1171-1173 (1995).
Cardillo et al., Enzymatic Resolution of alpha-Alkyl-beta-Amino Acids Using Immobilized Penicillin G Acylase, *J. Org. Chem.*, 61(24):8651-8654 (1996).
Falborg et al., "Asymmetric Titanium-Catalysed Michael Addition of O-Benzylhydroxylamine to alpha.beta-Unsaturated Carbonyl Compounds: Synthesis of beta-Amino Acid Precursors", *J. Chem. Soc. Perkin Trans. I*, (23):2823-2826 (1996).
Seebach et al., "Beta(2)- and Beta(3)-Peptides with Proteinaceous Side Chains: Synthesis and Solution Structures of Constitutional Isomers, a Novel Helical Secondary Structure and the Influence of Solvation and Hydrophobic Interactions on Folding," *Hel. Chim. Acta*, 81(5):932-982 (1998).
Sibi et al., "Chiral Lewis Acid Catalysis in Conjugate Additions of O-Benzylhydroxylamine to Unsaturated Amides. Enantioselective Synthesis of beta-Amino Acid Precursors," *J. Am. Chem. Soc.*, 120(26):6615-6616 (1998).
Myers et al., "Asymmetric Synthesis of beta-Amino Acid Derivatives via Catalytic Conjugate Addition of Hydrazoic Acid to Unsaturated Imides," *J. Am. Chem. Soc.*, 121(38):8959-8960 (1999).
Niu et al., "Concerted Conjugate Additionof Nucleophiles to Alkenoates. Part I: Mechanism of N-Alkylhydroxylamine Additions," *J. Am. Chem. Soc.*, 121(11):2456-2459 (1999).
Horstmann et al., "Asymmetric Conjugate Addition of Azide to Alpha,Beta-Unsaturated Carbonyl Compounds Catalyzed by Simple Peptides," *Angew. Chem. Int. Ed. Engl.*, 39(20):3635-3638 (2000).
Sibi et al., "N-Benzlhydroxylamine Addition to beta-Aryl Enolates. Enantioselective Synthesis of beta-Aryl-beta-Amino Acid Precursors," *Org. Lett.*, 2(21):3393-3396 (2000).
Sibi et al., "Enantioselective Conjugate Addition of Hydroxylamines to Pyrazolidinone Acrylamides," *Org. Lett.*, 3(26):4181-4184 (2001).
Sibi et al., "Enantioselective Conjugate Addition of Organomagnesium Amides to Enamidomalonates: Synthesis of Either Enantiomer of beta-Amino Acid Derivatives," *J. Am. Chem. Soc.*, 123(39):9708-9709 (2001).
Sibi et al., "Enantioselective Tandem Radical Reactions: Vicinal Difunctionalization in Acyclic Systems with Control over Relative and Absolute Stereochemistry," *J. Am. Chem. Soc.*, 123(38):9472-9473 (2001).
Goodman et al., A Practical Synthesis of alpha,beta-Unsaturated Imides, Useful Substrated For Asymmetric Conjugate Addition Reactions, *Adv. Synth. Catal.*, 344(9):953-956 (2002).
Liu et al., "Recent Advances in the Stereoselective Synthesis of beta-Amino Acids," *Tetrahedron*, 58(40):7991-8035 (2002).
Moglioni et al., "Reaction Between N-Alkylhydroxylamines and Chiral Enoate Esters: More Experimental Evidence for a Cycloaddition-Like Process, a Rationale Based on DFT Theoretical Calculations, and Stereoselective Synthesis of New Enantiopure beta-Amino Acids," *J. Org. Chem.*, 67(8):2402-2410 (2002).
Sibi et al.,, "The Role of the Achiral Template in Enantioselective Transformations. Radical Conjugate Additions to alpha-Methacrylates Followed by Hydrogen Atom Transfer," *J. Am. Chem. Soc.*, 124(6):984-991 (2002).
Wenzel et al., "Asymmetric Catalytic Mannich Reactions Catalyzed by Urea Derivatives: Enantioselective Synthesis of Beta-Aryl-Beta-amino Acids," *J. Am. Chem. Soc.*, 124(44):12964-12965 (2002).
Doi et al., "Chiral Ligand-Controlled Asymmetirc Conjugate Addition of Lithium Amides to Enoates," *J. Am. Chem. Soc.*, 125(10):2886-2887 (2003).
Sibi et al., "Enantioselective Synthesis of alpha,beta-Disubstituted-beta-Amino Acids," *J. Am. Chem. Soc.*, 125(39):11796-11797 (2003).
Sibi et al., "Enantioselective H-Atom Transfer Reactions: A New Methodology for the Synthesis of beta2-Amino Acids," *Angew. Chem. Int. Ed.*, 43(10):1235-1238 (2004).

(Continued)

*Primary Examiner* — Daniel Sullivan
*Assistant Examiner* — Yevegeny Valenrod
(74) *Attorney, Agent, or Firm* — Mueting, Raasch & Gebhardt, P.A.

(57) ABSTRACT

Disclosed are β-amino acids that are unsubstituted in the β position; that are substituted in the β position with an aryl group; that are substituted in the α position with an aryl group; that bear two substituents in the α position; and/or that are substituted in the α and β positions with groups which, together with the carbon atoms at the α and β positions, form a ring. Also disclosed are methods for making the above-mentioned β-amino acids and other β-amino acids which involve providing an α,β-unsaturated imide; converting the α,β-unsaturated imide to a 2-substituted-isoxazolidin-5-one; and converting the 2-substituted-isoxazolidin-5-one to a β-amino acid.

51 Claims, No Drawings

OTHER PUBLICATIONS

Corminboeuf et al., "Chiral relay: a novel strategy for the control and amplification of enantioselectivty in chiral Lewis Acid promoted reactions," Jan. 3, 2003 *Chem. Eur. J.* 9(1):28-35. Avalable online on Dec. 18, 2002.

Luesch et al., "Ulongamides A—F, new β-amino acid-contaning Cyclodepsipeptides from Palauan collections of the marine cyanobacterium *Lyngbya* sp.," Jul. 2002 *J. Nat. Prod.* 65(7):996. Available online on Jun. 25, 2002.

Miyata et al., "Sterospecific nucleophilic addition reactions to olefins. Addition of thiols to α,β-unsaturated carboxylic acid derivatives," Nov. 1991 *J. Org. Chem.* 56(23):6556.

Mynderse et al., "57-Normajusculamide C, a minor cyclic depsipeptide isolated from *Lyngbya majuscula*," Nov. 1998 *J. Nat. Prod.* 51(6):12991301.

Sibi et al., "Practical and efficent enantioselective conjugate radical additions," Jun. 13, 1997 *J. Org. Chem.* 62(12):3800-3801.

Sibi et al., "A new methodology for the synthesis of β-amino acids," 2000 *J. Chem. Soc., Perkin Trans.* 2000:1461-1466.

Sibi et al., "Enantioselective conjugate additions," Oct. 6, 2000 *Tetrahedron* 56(41):8033-8061. Avalable online on Sep. 28, 2000.

Sibi et al., "Reversal of stereochemistry in enantioselective transformations. Can they be planned or are they just accidental?" Jul. 2001 *Curr. Org. Chem.* 5(7):719-755.

Sibi et al., "A new approach to enantiocontrol and enantioselectivity amplification: chiral relay in Diels—Alder reactions," Aug. 29, 2001 *J. Am. Chem. Soc.* 123(34):8444-8445. Available online on Aug. 7, 2001.

Sibi et al., "Enantioselective conjugate addition of silylketene acetals to β-enamidomalonates. Synthesis of β-amino acids derivatives," Aug. 22, 2002 *Org. Lett.* 4(17):2933-2936. Available online on Aug. 2, 2002.

Sibi et al., "Temperature dependent reversal of sterochemistry in enantioselective conjugate amine additions," Oct. 7, 2002 *Tetrahedron* 58(41):8357-8363. Available online on Sep. 28, 2002.

Sibi et al., Oct. 1, 2003 *J. Am. Chem. Soc.* 125(39):11796-11797; Supplemental Information available online [retrieved on May 24, 2011]. Retrieved from the Internet: <http://pubs.acs.org/doi/suppl/10.1021/ja0372309/suppl_file/ja0372309si20030809_034150.pdf>; 18 pgs.

Sundararajan et al., "A new polymer-anchored chiral catalyst for asymmetric Michael Addition reactions," 2001 *Org. Lett.* 3(3):389-392. Available online on Jan. 6, 2001.

* cited by examiner

US 8,034,974 B2

BETA-AMINO ACIDS AND METHODS INTERMEDIATES FOR MAKING SAME

The present application claims the benefit of U.S. Provisional Patent Application Ser. No. 60/488,947, filed Jul. 21, 2003, which provisional patent application is hereby incorporated by reference.

The present invention was made, at least in part, with the support of National Science Foundation/EPSCoR Grant No. EPS-0132289, with the support of National Science Foundation Grant No. CHE-9983680, and with the support of National Science Foundation Grant No. CHE-0316203. The Federal Government has certain rights in this invention.

FIELD OF THE INVENTION

The present invention relates to amino acids and to methods and intermediates for making same and, more particularly, to beta amino acids and to methods and intermediates for making same.

BACKGROUND OF THE INVENTION

There has been an increasing interest in β-amino acids and peptides derived from them, and, more particularly, in optically active β-amino acids and peptides derived from such optically active β-amino acids. Optically active β-amino acids include a number of naturally occurring substances in the free form with an interesting pharmacological profile. Functionalized β-amino acids are important segments of bioactive molecules. For example, TAXOL™ contains a phenylisoserine side chain as a key pharmacophore, and compounds of cyclic β-amino acids make up the class of β-lactam antibiotics. Additionally, β-amino acids are components of peptidic natural products with a wide range of biological activity. Peptides consisting of β-amino acids have promising pharmaceutical use as orally active drugs since they are hydrolytically stable. Given the significance of the β-amino acids, development of new methodologies for their synthesis, especially for the stereoselective synthesis of chiral β-amino acids, is important.

Accordingly, in view of the potential pharmaceutical utility of β-amino acids and β peptides, there is a continuing need for methods for the preparation of β-amino acids, especially β-amino acids in optically active form, and the present invention is directed, in part, to addressing this need.

SUMMARY OF THE INVENTION

The present invention relates to a method for making β-amino acids. The method includes providing an α,β-unsaturated imide; converting the α,β-unsaturated imide to a 2-substituted-isoxazolidin-5-one; and converting the 2-substituted-isoxazolidin-5-one to a β-amino acid.

The present invention also relates to a β-amino acid that is unsubstituted in the β position; that is substituted in the β position with an aryl group; that is substituted in the α position with an aryl group; that bears two substituents in the α position; and/or that is substituted in the α and β positions with groups which, together with the carbon atoms at the α and β positions, form a ring.

The present invention also relates to a method for making β-amino acids that are substituted in the α position, that are unsubstituted in the β position, and/or that bear an aryl substituent in the β position. The method includes providing an appropriate α,β-unsaturated imide, and converting the α,β-unsaturated imide to a β-amino acid.

The present invention also relates to a method for making a β-amino acid that is unsubstituted in the α position; that is substituted in the β position with an aryl group; that is substituted in the α position with an aryl group; that bears two substituents in the α position; and/or that is substituted in the α and β positions with groups which, together with the carbon atoms at the α and β positions, form a ring. The method includes providing an appropriate 2-substituted-isoxazolidin-5-one, and converting the 2-substituted-isoxazolidin-5-one to a β-amino acid.

The present invention also relates to a method for making a 2-substituted-isoxazolidin-5-one. The method includes providing an α,β-unsaturated imide and cyclizing the α,β-unsaturated imide under conditions effective to produce the 2-substituted-isoxazolidin-5-one.

The present invention also relates to 2-substituted-isoxazolidin-5-ones that are unsubstituted in the 3 position; that are substituted in the 3 position with an aryl group; that are substituted in the 4 position with a non-methyl substituent; that are 4,4-disubstituted; and/or that are substituted in the 3 and 4 positions with groups which, together with the carbon atoms at the 3 and 4 positions, form a ring.

The present invention also relates to α,β-unsaturated imides that are substituted in the α position.

DETAILED DESCRIPTION OF THE INVENTION

The present invention relates to a β-amino acid that is unsubstituted in the β position; that is substituted in the β position with an aryl group; that is substituted in the α position with an aryl group; that bears two substituents in the α position; and/or that is substituted in the α and β positions with groups which, together with the carbon atoms at the α and β positions, form a ring.

As used herein, "β-amino acid" is meant to refer to any compound which has a carboxylic acid group and an amine function that are separated by exactly two carbon atoms (e.g., an alkylene group having the formula —C(R)(R')—CH(R")— where each of R, R', and R" is independently selected from, for example, a hydrogen atom, a non-hydrogen atom, an alkyl group, and an aryl group or where R and R", together with the carbon atoms to which they are attached combine to form a 5-12 membered ring). The nature of the β-amino acid's carboxylic acid group is not particularly critical to the practice of the present invention: it can be, illustratively, a free carboxylic acid group (—COOH), a carboxylic acid salt group, a carboxylic acid ester group, a carboxylic acid amide group, a carboxylic acid imide group, and the like. The nature of the β-amino acid's amine function is not particularly critical to the practice of the present invention: it can be, illustratively, an unsubstituted amine group (i.e., an —NH$_2$ group); a monosubstituted amine group; or a disubstituted amine group, which substituents can be the same or different or which substituents can combine (together with the nitrogen atom) to form a substituted or unsubstituted ring or ring system (e.g., a substituted or unsubstituted piperidino ring, a substituted or unsubstituted morpholino ring, or another substituted or unsubstituted 5-12 membered ring or ring system).

As one skilled in the art will note, generally speaking, the α position of a β-amino acid can be unsubstituted (i.e., two hydrogen atoms are present at the α position), or it can be substituted, e.g., as in the case where the α position is monosubstituted (i.e., one hydrogen atom is present at the α position and one non-hydrogen atom or group is present at the α position) or disubstituted (i.e., no hydrogen atoms are present at the α position and two non-hydrogen atoms or groups are present at the α position). Likewise, the β position of a β-amino acid can be unsubstituted (i.e., two hydrogen atoms are present at the β position), or it can be substituted, e.g., as in the case where the β position is monosubstituted (i.e., one hydrogen atom is present at the β position and one non-hydrogen atom or group is present at the β position) or disubstituted (i.e., no hydrogen atoms are present at the β position and two non-hydrogen atoms or groups are present at the β position).

As discussed above, the present invention relates to a β-amino acid that is unsubstituted in the β position. Illustratively, such β-amino acids are meant to include α-substituted-β-unsubstituted-β-amino acids, such as α-monosubstituted-β-unsubstituted-β-amino acids and α,α-disubstituted-β-unsubstituted-β-amino acids. The α substituent or substituents of the aforementioned α-monosubstituted-β-unsubstituted-β-amino acids and α,α-disubstituted-β-unsubstituted-β-amino acids can be selected from an alkyl group, an aryl group, a hydroxy group, an alkoxy group (which is meant to include aryloxy groups, e.g., phenoxy groups), other groups having the formula —OP (where P is a hydroxy protecting moiety, such as where —OP represents —O—COR, —O—SiR$_3$, etc., where each R independently represents a substituted or unsubstituted alkyl or aryl group), a thiol group, an alkylthio group, an arylthio group, an amine group (which is meant to include unsubstituted, monosubstituted, and disubstituted (e.g., with aryl or alkyl groups) amine groups), a carboxylic acid group (which is meant to include COOH groups as well as carboxylic acid derivatives, e.g., carboxylic acid esters, amides, etc.), a phosphine group, a sulfonic acid group, and a halogen atom (e.g., F, Cl, Br, and I).

As used herein, "alkyl" is meant to include linear alkyls, branched alkyls, and cycloalkyls, each of which can be substituted or unsubstituted. "Alkyl" is also meant to include lower linear alkyls (e.g., C1-C6 linear alkyls), such as methyl, ethyl, n-propyl, n-butyl, n-pentyl, and n-hexyl; lower branched alkyls (e.g., C3-C8 branched alkyls), such as isopropyl, t-butyl, 1-methylpropyl, 2-methylpropyl, 1-methylbutyl, 2-methylbutyl, 3-methylbutyl, 1,2-dimethylpropyl, 1,1-dimethylpropyl, 2,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 2-methyl-2-ethylpropyl, 2-methyl-1-ethylpropyl, and the like; and lower cycloalkyls (e.g., C3-C8 cycloalkyls), such as cyclopropyl, cyclobutyl, cyclopentyl, cyclohexyl, and the like. "Alkyl", as use herein, is meant to include unsubstituted alkyls, such as those set forth above, in which no atoms other than carbon and hydrogen are present. "Alkyl", as use herein, is also meant to include substituted alkyls. Suitable substituents include aryl groups (which may themselves be substituted), as in the case where the "alkyl" is a phenyl-substituted methyl group (e.g., a benzyl moiety). Other suitable substituents include heterocyclic rings (saturated or unsaturated and optionally substituted), hydroxy groups, alkoxy groups (which is meant to include aryloxy groups (e.g., phenoxy groups)), thiol groups, alkylthio groups, arylthio groups, amine groups (which is meant to include unsubstituted, monosubstituted, or disubstituted (e.g., with aryl or alkyl groups) amine groups), carboxylic acid groups (which is meant to include COOH groups as well as carboxylic acid derivatives, e.g., carboxylic acid esters, amides, etc.), phosphine groups, sulfonic acid groups, halogen atoms (e.g., F, Cl, Br, and I), and the like. Further, alkyl groups bearing one or more alkenyl or alkynyl substituents (e.g., a methyl group itself substituted with a prop-1-en-1-yl group to produce a but-2-en-1-yl substituent or a methyl group itself substituted with a vinyl group to produce an allyl substituent) is meant to be included in the meaning of "alkyl".

As used herein, "aryl" is meant to include aromatic rings, preferably having from 4 to 12 members, such as phenyl rings. These aromatic rings can optionally contain one or more heteroatoms (e.g., one or more of N, O, and S), and, thus, "aryl", as used herein, is meant to include heteroaryl moieties, such as pyridyl rings and furanyl rings. The aromatic rings can be optionally substituted. "Aryl" is also meant to include aromatic rings to which are fused one or more other aryl rings or non-aryl rings. For example, naphthyl groups, benzimidazole groups, and 5,6,7,8-tetrahydro-2-naphthyl groups (each of which can be optionally substituted) are aryl groups for the purposes of the present application. As indicated above, the aryl rings can be optionally substituted. Suitable substituents include alkyl groups (which can optionally be substituted), other aryl groups (which may themselves be substituted), heterocyclic rings (saturated or unsaturated), hydroxy groups, alkoxy groups (which is meant to include aryloxy groups (e.g., phenoxy groups)), thiol groups, alkylthio groups, arylthio groups, amine groups (unsubstituted, monosubstituted, or disubstituted, e.g., with aryl or alkyl groups), carboxylic acid groups, carboxylic acid derivatives (e.g., carboxylic acid esters, amides, etc.), phosphine groups, sulfonic acid groups, halogen atoms (e.g., F, Cl, Br, and I), and the like.

As used herein, "alkoxy" is meant to include groups having the formula —O—R, where R is an alkyl or aryl group. They include methoxy, ethoxy, propoxy, benzyloxy, phenoxy, 4-methylphenoxy, and the like.

As used herein, "ring" refers to a homocyclic or heterocyclic ring which can be saturated or unsaturated. The ring can be unsubstituted, or it can be substituted with one or more substituents. The substituents can be saturated or unsaturated, aromatic or nonaromatic, and examples of suitable substituents include those recited above in the discussion relating to substituents on alkyl and aryl groups. Furthermore, two or more ring substituents can combine to form another ring, so that "ring", as used herein, is meant to include fused ring systems. In the case where the ring is saturated (i.e., in the case where each of the atoms making up the ring is joined by single bonds to other members of the ring), the ring may optionally include unsaturated (aromatic or nonaromatic) or saturated substituents.

"Halogen", as used herein is meant to include fluorine, chlorine, bromine, and iodine.

Returning to our discussion of the β-unsubstituted-β-amino acids of the present invention, and more particularly, to our discussion of α-substituted-β-unsubstituted-β-amino acids, examples of such α-substituted-β-unsubstituted-β-amino acids of the present invention include α-substituted-β-unsubstituted-β-amino acids in which the α position is monosubstituted, for example, with an alkyl group (e.g., a methyl group or other C1-C6 alkyl group). As further illustration, β-unsubstituted-β-amino acids of the present invention include those having the following formula ("Formula I"):

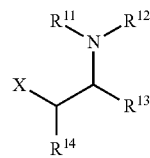

where $R^{11}$ and $R^{12}$ are independently selected from H, an alkyl group, and an aryl group or $R^{11}$ and $R^{12}$, together with the nitrogen atom to which they are bonded, form a ring; where $R^{13}$ is a hydrogen atom; where $R^{14}$ is selected from a hydrogen atom, an alkyl group, an aryl group, a hydroxy group, an alkoxy group, other groups having the formula —OP (P representing a hydroxy protecting moiety), a thiol group, an alkylthio group, an arylthio group, an amine group, a carboxylic acid group, a phosphine group, a sulfonic acid group, and a halogen atom; and where X is a carboxylic acid group. In one embodiment, $R^{14}$ is not hydrogen; in another embodiment, $R^{14}$ is an alkyl group; in yet another embodiment, $R^{14}$ is an aryl group; in still another embodiment, $R^{14}$ is a methoxy group or another alkoxy group; and in still another embodiment, $R^{14}$ is a fluorine atom or another halogen atom.

As briefly discussed above, the present invention also relates to a β-amino acid that is substituted in the β position with an aryl group, such as a phenyl group, a 3-furanyl group or other furanyl group, a 3,4-methylenedioxyphenyl group, and the like. Examples of such β-amino acids that are substituted in the β position with an aryl group include α-unsubstituted-β-aryl-β-amino acids as well as α-substituted-β-aryl-β-amino acids (such as α-monosubstituted-β-aryl-β-amino acids and α,α-disubstituted-β-aryl-β-amino acids). The α substituent or substituents of the aforementioned α-monosubstituted-β-aryl-β-amino acids and α,α-disubstituted-β-aryl-β-amino acids can be selected from an alkyl group, an aryl group, a hydroxy group, a methoxy or other alkoxy group, other groups having the formula —OP (P representing a hydroxy protecting moiety), a thiol group, an alkylthio group, an arylthio group, an amine group, a carboxylic acid group, a phosphine group, a sulfonic acid group, and a fluorine or other halogen atom. Further examples of such β-amino acids that are substituted in the β position with an aryl group include α-substituted-β-substituted-β-amino acids bearing an alkyl substituent in the α position, α-substituted-β-substituted-β-amino acids bearing an aryl substituent in the α position, α-substituted-β-substituted-β-amino acids bearing an alkoxy substituent in the α position, α-substituted-β-substituted-β-amino acids bearing a halogen atom substituent in the α position, and α-substituted-β-substituted-β-amino acids bearing a fluorine atom substituent in the α position. As further illustration, β-amino acids that are substituted in the β position with an aryl group of the present invention include those having Formula I where $R^{11}$ and $R^{12}$ are independently selected from H, an alkyl group, and an aryl group or $R^{11}$ and $R^{12}$, together with the nitrogen atom to which they are bonded, form a ring; where $R^{13}$ is an aryl group; where $R^{14}$ is selected from a hydrogen atom, an alkyl group, an aryl group, a hydroxy group, an alkoxy group, other groups having the formula —OP (P representing a hydroxy protecting moiety), a thiol group, an alkylthio group, an arylthio group, an amine group, a carboxylic acid group, a phosphine group, a sulfonic acid group, and a halogen atom; and where X is a carboxylic acid group. In one embodiment, $R^{14}$ is not hydrogen; in another embodiment, $R^{14}$ is an alkyl group; in still another embodiment, $R^{14}$ is an aryl group; in still another embodiment, $R^{14}$ is a methoxy or another alkoxy group; in still another embodiment, $R^{14}$ is a fluorine atom or another halogen atom; in yet another embodiment, $R^{13}$ is a phenyl group; in yet another embodiment, $R^{13}$ is a furanyl group; in yet another embodiment, $R^{13}$ is a 3-furanyl group; and in yet another embodiment, $R^{13}$ is a 3,4-methylenedioxyphenyl group.

As briefly discussed above, the present invention also relates to a β-amino acid that is substituted in the α position with an aryl group, such as a phenyl group. Examples of such β-amino acids that are substituted in the α position with an aryl group include α-aryl-β-unsubstituted-β-amino acids and α-aryl-β-substituted-β-amino acids (e.g., α-aryl-β-monosubstituted-β-amino acids). β substituents of the aforementioned α-aryl-β-substituted-β-amino acids (e.g., α-aryl-βmonosubstituted-β-amino acids) can be selected from a methyl group or other alkyl group, a phenyl group or other aryl group, and a carboxylic acid group other than COOH. Further examples of such β-amino acids that are substituted in the α position with an aryl group include α-aryl-β-aryl-β-amino acids, α-aryl-β-alkyl-β-amino acids, and α-aryl-β-unsubstituted-β-amino acids. As further illustration, β-amino acids that are substituted in the α position with an aryl group of the present invention include those having Formula I where $R^{11}$ and $R^{12}$ are independently selected from H, an alkyl group, and an aryl group or $R^{11}$ and $R^{12}$, together with the nitrogen atom to which they are bonded, form a ring; where $R^{13}$ is selected from a hydrogen atom, an alkyl group, an aryl group, and a carboxylic acid group other than COOH; where $R^{14}$ is an aryl group; and where X is a carboxylic acid group. In one embodiment, $R^{13}$ is a hydrogen atom; in another embodiment, $R^{13}$ is an alkyl group; in still another embodiment, $R^{13}$ is a C1-C6 alkyl group; in still another embodiment, $R^{13}$ is a methyl group; and in yet another embodiment, $R^{13}$ is a phenyl or other aryl group.

As briefly discussed above, the present invention also relates to a β-amino acid that bears two substituents in the α position. Examples of such β-amino acids that bear two substituents in the α position include α,α-disubstituted-β-substituted-β-amino acids (e.g., α,α-disubstituted-β-monosubstituted-β-amino acids). The α substituents can be the same or different and they can be selected from, for example, an alkyl group, an aryl group, a hydroxy group, an alkoxy group, other groups having the formula —OP (P representing a hydroxy protecting moiety), a thiol group, an alkylthio group, an arylthio group, an amine group, a carboxylic acid group, a phosphine group, a sulfonic acid group, and a halogen atom. Examples of such α,α-disubstituted-β-substituted-β-amino acids include α,α-disubstituted-β-alkyl-β-amino acids, α,α-disubstituted-β-methyl-β-amino acids; α,α-disubstituted-β-amino acids bearing two alkyl groups in the α position; α,α-disubstituted-β-amino acids bearing two alkyl groups in the α position, at least one of which α alkyl groups is a methyl group; α,α-disubstituted-β-alkyl-β-amino acids bearing two alkyl groups in the α position, at least one of which α alkyl groups is a methyl group; α,α-disubstituted-β-methyl-β-amino acids bearing two alkyl groups in the α position, at least one of which α alkyl groups is a methyl group; α,α-disubstituted-β-amino acids bearing two alkyl groups in the α position, at least one of which α alkyl groups is a methyl group and the other of which α alkyl groups is selected from a methyl group, an allyl group, and a benzyl group; α,α-disubstituted-β-alkyl-β-amino acids bearing two alkyl groups in the α position, at least one of which α alkyl groups is a methyl group and the other of which α alkyl groups is selected from a methyl group, an allyl group, and a benzyl group; and α,α-disubstituted-β-methyl-β-amino acids bearing two alkyl groups in the α position, at least one of which α alkyl groups is a methyl group and the other of which α alkyl groups is selected from a methyl group, an allyl group, and a benzyl group. As further illustration, β-amino acids that bear two substituents in the α position of the present invention include those having the following formula ("Formula II"):

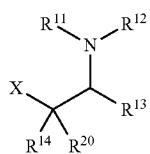

where $R^{11}$ and $R^{12}$ are independently selected from H, an alkyl group, and an aryl group or $R^{11}$ and $R^{12}$, together with the nitrogen atom to which they are bonded, form a ring; where $R^{13}$ is selected from a hydrogen atom, an alkyl group, an aryl group, and a carboxylic acid group other than COOH; where $R^{14}$ and $R^{20}$ are independently selected from an alkyl group, an aryl group, a hydroxy group, an alkoxy group, other groups having the formula —OP (P representing a hydroxy protecting moiety), a thiol group, an alkylthio group, an arylthio group, an amine group, a carboxylic acid group, a phosphine group, a sulfonic acid group, and a halogen atom; and where X is a carboxylic acid group. In one embodiment, $R^{13}$ is not hydrogen; in another embodiment, $R^{13}$ is an alkyl group; in yet another embodiment, $R^{13}$ is a C1-C6 alkyl group; in yet another embodiment, $R^{13}$ is a methyl group; in still another embodiment, each of $R^{14}$ and $R^{20}$ independently represent an alkyl group; in still another embodiment, $R^{14}$ is a methyl group and $R^{20}$ is an alkyl group; in still another embodiment, $R^{13}$ is an alkyl group, $R^{14}$ is a methyl group, and $R^{20}$ is an alkyl group; in still another embodiment, $R^{13}$ is an methyl group, $R^{14}$ is a methyl group, and $R^{20}$ is an alkyl group; in still another embodiment, $R^{14}$ is a methyl group and $R^{20}$ is a methyl group, an allyl group, or a benzyl group; in still another embodiment, $R^{13}$ is an alkyl group, $R^{14}$ is a methyl group, and $R^{20}$ is a methyl group, an allyl group, or a benzyl group; and in still another embodiment, $R^{13}$ is an methyl group, $R^{14}$ is a methyl group, and $R^{20}$ is a methyl group, an allyl group, or a benzyl group.

As briefly discussed above, the present invention also relates to a β-amino acid that is substituted in the α and β positions with groups which, together with the carbon atoms at the α and β positions, form a ring, such as a substituted or unsubstituted, heterocyclic or homocyclic, saturated or unsaturated ring or ring system, (e.g., a substituted or unsubstituted cycloalkyl ring or another substituted or unsubstituted 5-, 6-, 7-, 8-, 9-, 10-, 11-, or 12-membered ring or ring system). Examples of such β-amino acids include those having the formula ("Formula III"):

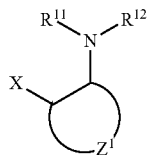

where $R^{11}$ and $R^{12}$ are independently selected from H, an alkyl group, and an aryl group or $R^{11}$ and $R^{12}$, together with the nitrogen atom to which they are bonded, form a ring; where $Z^1$ represents a moiety which, together with the nitrogen atom and carbon atom to which it is bonded, forms a ring (e.g., a substituted or unsubstituted, homocyclic or heterocyclic, saturated or unsaturated, 5-, 6-, 7-, 8-, 9-, 10-, 11-, or 12-membered ring); and where X is a carboxylic acid group. Illustratively, $Z^1$ can be a substituted or unsubstituted prop-1,3-diyl moiety (e.g., a —CH$_2$—CH$_2$—CH$_2$— moiety) or a but-1,4-diyl moiety (e.g., a —CH$_2$—CH$_2$—CH$_2$—CH$_2$— moiety). As further illustration, $Z^1$ can be a moiety having the formula —CH$_2$—Z$^2$—CH$_2$—, where $Z^2$ represents a heteroatom, such as an oxygen atom (—O—), a sulfur atom (—S—), a nitrogen atom bearing a hydrogen (—NH—), or a substituted nitrogen atom (e.g., —NR—, where R is, for example, an alkyl group, an aryl group, or an amine protecting group).

As one skilled in the art will appreciate, the β-amino acids of the present invention can have one or more chiral centers, and the β-amino acids can be substantially chirally pure as to none, one, more than one, or all of these chiral centers. For example, α-monosubstituted-β-monosubstituted amino acids (e.g., bearing an aryl group at the α position and an aryl or alkyl group at the β position) will have at least two chiral centers (i.e., one at the α carbon and another at the β carbon). The α-monosubstituted-β-monosubstituted amino acids can be racemic as to both of these chiral centers; or the α-monosubstituted-β-monosubstituted amino acids can be substantially chirally pure as to one or both of these chiral centers. As used herein, chiral center A is to be deemed to be "substantially chirally pure" if (i) chiral center A in more than 50% (e.g., more than about 55%, more than about 60%, more than about 65%, more than about 70%, more than about 75%, more than about 80%, more than about 85%, and/or more than about 90%) of the β-amino acid molecules is in the R-form or (ii) chiral center A in more than 50% (e.g., more than about 55%, more than about 60%, more than about 65%, more than about 70%, more than about 75%, more than about 80%, more than about 85%, and/or more than about 90%) of the β-amino acid molecules is in the S-form. Additionally or alternatively, the β-amino acids of the present invention can be substantially pure (i.e., substantially free of materials which are not classifiable as β-amino acids). In this regard, the β-amino acids of the present invention are to be considered as being substantially pure if the β-amino acids make up more than about 25% (e.g., more than about 30%, more than about 40%, more than about 50%, more than about 60%, more than about 70%, more than about 75%, more than about 80%, more than about 85%, and/or more than about 90%), by weight, of all of the materials present with the β-amino acids.

The aforedescribed β-amino acids of the present invention, as well as other β-amino acids, can be prepared by the methods described hereinbelow.

The present invention also relates to a method for making β-amino acids. The method includes providing an α,β-unsaturated imide; converting the α,β unsaturated imide to a 2-substituted-isoxazolidin-5-one; and converting the 2-substituted-isoxazolidin-5-one to a β-amino acid. The method of the present invention can be used to prepare a variety of β-amino acids. For example, the method can be used to prepare β-amino acids of the present invention, as described hereinabove (i.e., β-amino acids that are unsubstituted in the β position; that are substituted in the β position with an aryl group; that are substituted in the α position with an aryl group; that bear two substituents in the α position; and/or that are substituted in the α and β positions with groups which, together with the carbon atoms at the α and β positions, form a ring). The method of the present invention can be also be used to prepare other β-amino acids. Illustratively, the method of the present invention can be used to prepare α-substituted-β-amino acids and β substituted-β-amino acids. Examples of α-substituted-β-amino acids include α-monosubstituted-β-amino acids and α,α-disubstituted-β-amino acids, which can be unsubstituted at the β position (e.g., α-monosubstituted-unsubstituted-β-amino acids and α,α-disubstituted-unsubstituted-β-amino acids), monosubstituted at the β position (e.g., α-monosubstituted-β-monosubstituted-β-amino acids and α,α-disubstituted-β-monosubstituted-β-amino acids), or disubstituted at the β position (e.g., α-monosubstituted-β,β-disubstituted-β-amino acids and α,α-disubstituted-β,β-disubstituted-β-amino acids). Examples of β-substituted-β-amino acids include β-monosubstituted-β-amino acids and β,β-disubstituted-β-amino acids, which can be unsubstituted at the α position (e.g., α-unsubstituted-β-monosubstituted-β-amino acids and α-unsubstituted-β,βdisubstituted-β-amino acids), monosubstituted at the α position (e.g., α-monosubstituted-β-monosubstituted-β-amino acids and α-monosubstituted-β,β-disubstituted-β-amino acids), or disubstituted at the α position (e.g., α,α-disubstituted-β-monosubstituted-β-amino acids and α,α-disubstituted-β,β-disubstituted-β-amino acids). As further illustration, the method of the present invention can be used to prepare α-substituted-β-substituted-β-amino acids, which is meant to include α-monosubstituted-β-monosubstituted-β-amino acids, α,α-disubstituted-β-monosubstituted-β-amino acids, α-monosubstituted-β,β-disubstituted-β-amino acids, and α,α-disubstituted-β,β-disubstituted-β-amino acids.

In certain aspects of the method of the present invention, the method can be used to prepare α-monosubstituted-β-amino acids which are substituted at the α position with one hydrogen atom and one aryl group, such as a substituted or unsubstituted phenyl group or a substituted or unsubstituted aromatic heterocyclic group. In certain other aspects of the method of the present invention, the method can be used to prepare α-monosubstituted-β-monosubstituted-β-amino acids which are substituted at the α position with one hydrogen atom and one aryl group (e.g., a substituted or unsubstituted phenyl group or a substituted or unsubstituted aromatic heterocyclic group) and which are substituted at the β position with one hydrogen atom and one aryl group (e.g., a substituted or unsubstituted phenyl group or a substituted or unsubstituted aromatic heterocyclic group), which aryl substituent at the β position can be the same as or different than the aryl substituent at the α position). In certain other aspects of the method of the present invention, the method can be used to prepare α-monosubstituted-β-amino acids which are substituted at the α position with one hydrogen atom and one non-hydrogen, non-methyl substituent, such as a substituted methyl group (e.g., a benzyl group or a chloromethyl group), a substituted or unsubstituted C2-C3 linear alkyl group, a substituted or unsubstituted C4-C6 linear alkyl group, a substituted or unsubstituted branched alkyl group, or a substituted or unsubstituted cyclic alkyl group. In certain other aspects of the method of the present invention, the method can be used to prepare α-monosubstituted-β-monosubstituted-β-amino acids which are substituted at the α position with one hydrogen atom and one non-hydrogen, non-methyl substituent, such as a substituted methyl group (e.g., a benzyl group or a chloromethyl group), a substituted or unsubstituted C2-C3 linear alkyl group, a substituted or unsubstituted C4-C6 linear alkyl group, a substituted or unsubstituted branched alkyl group, or a substituted or unsubstituted cyclic alkyl group, and which are substituted at the β position with one hydrogen atom and one aryl group (e.g., a substituted or unsubstituted phenyl group or a substituted or unsubstituted aromatic heterocyclic group).

In still other aspects of the method of the present invention, the method can be used to prepare α-substituted-β-amino acids, α-substituted-β-amino acids bearing an alkyl substituent in the α position, α-substituted-β-amino acids bearing an aryl substituent in the α position, α-substituted-β-amino acids bearing an alkoxy substituent in the α position, α-substituted-β-amino acids bearing a halogen atom substituent in the α position, α-substituted-β-amino acids bearing a fluorine atom substituent in the α position, α,α-disubstituted-β-amino acids, β-unsubstituted-β-amino acids, α-substituted-β-unsubstituted-β-amino acids, β-substituted-β-amino acids bearing an aryl substituent in the β position, α-substituted-β-substituted-β-amino acids, α-substituted-β-substituted-β-amino acids bearing an aryl substituent in the β position, α-substituted-β-substituted-β-amino acids bearing an aryl substituent in the α position, and/or α-substituted-β-substituted-β-amino acids bearing an aryl substituent in the α position and an aryl substituent in the β position.

As discussed above, the method of the present intention includes providing an α,β unsaturated imide; converting the α,β unsaturated imide to a 2-substituted-isoxazolidin-5-one; and converting the 2-substituted-isoxazolidin-5-one to a β-amino acid.

A variety of α,β-unsaturated imides can be used in the practice of the method of the present invention, the choice being governed, primarily, by the desired substitution pattern on the β-amino acid product. Illustratively, β-amino acids having Formula I:

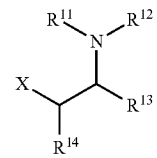

can be prepared from α,β unsaturated imides having the following formula ("Formula IV"):

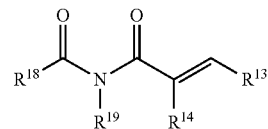

In the aforementioned Formulae I and IV, $R^{11}$ and $R^{12}$ can be independently selected from H, an alkyl group, and an aryl group, or $R^{11}$ and $R^{12}$, together with the nitrogen atom to which they are bonded, form a ring; $R^{13}$ can be selected from a hydrogen atom, an alkyl group, an aryl group, and a carboxylic acid group other than COOH; $R^{14}$ can be selected from a hydrogen atom, an alkyl group, an aryl group, a hydroxy group, an alkoxy group, other groups having the formula —OP (P representing a hydroxy protecting moiety), a thiol group, an alkylthio group, an arylthio group, an amine group, a carboxylic acid group, a phosphine group, a sulfonic acid group, and a halogen atom; or $R^{13}$ and 14, together with the carbon atoms to which they are bonded, can form a ring; X can be a carboxylic acid group; $R^{18}$ can be a substituted or unsubstituted alkyl group, a substituted or unsubstituted aryl group, or an alkoxy group; $R^{19}$ can be a hydrogen atom, a substituted or unsubstituted alkyl group, or a substituted or unsubstituted aryl group; or $R^{18}$ and $R^{19}$, together with the atoms to which they are bonded, can form a ring.

The aforementioned α,β-unsaturated imides can be conveniently prepared from the corresponding α,β-unsaturated carboxylic acid and carboxamide by conversion of the α,β unsaturated carboxylic acid to its acid chloride (e.g., using an equimolar amount or slight molar excess of oxalyl chloride in an appropriate solvent, such as dry $CH_2Cl_2$ or other chlorinated hydrocarbon solvent, at about room temperature for from about 30 minutes to about 24 hours, such as for about 2 hours) followed by reaction of the α,β-unsaturated carboxylic acid chloride with the carboxamide. Illustratively, α,β-unsaturated imides of Formula IV can be prepared from α,β-unsaturated carboxylic acids having the following formula:

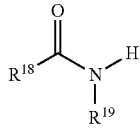

and carboxamides having the formula:

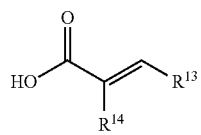

Once the α,β-unsaturated imide is provided, it is converted to a 2-substituted-isoxazolidin-5-one. The conversion can be carried out, for example, using a substituted hydroxyl amine and a Lewis acid. Suitable substituted hydroxyl amines include alkyl hydroxyl amines and aryl hydroxyl amines. Illustratively, the substituted hydroxyl amine can have the formula $R^{16}$—NHOH, where $R^{16}$ is a substituted or unsubstituted aryl group or a substituted or unsubstituted alkyl group (e.g., a benzyl group or another aryl substituted methyl group). The Lewis acid salt can be, for example, a magnesium Lewis acid salt, a zinc Lewis acid salt, a copper Lewis acid salt, an iron(II) or iron(III) Lewis acid salt, a rare earth metal Lewis acid salt, an yttrium Lewis acid salt, an ytterbium Lewis acid salt, a Lewis acid triflate salt (e.g., $Mg(OTf_2)_2$), a Lewis acid perchlorate salt (e.g., $Mg(ClO_4)_2$), and/or a Lewis acid triflimide salt (e.g., $Mg(NTf_2)_2$). Suitable Lewis acids also include chiral Lewis acid complexes, such as those derived from a magnesium salt (e.g., $Mg(NTf_2)_2$, $Mg(ClO_4)_2$, etc.) and a chiral ligand, e.g., a chiral bisoxazoline ligand having, for example, one of the following formulae:

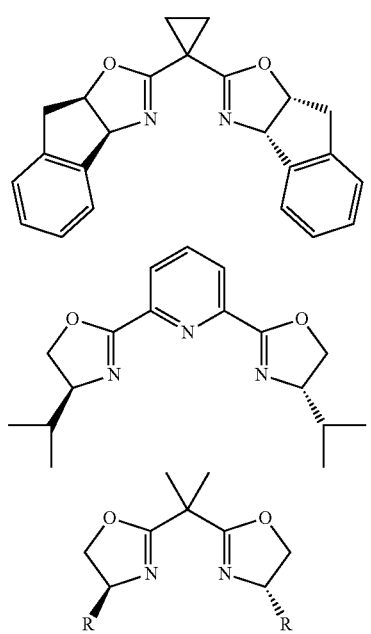

where R is benzyl, isopropyl, isobutyl, t-butyl, or phenyl. These and other suitable chiral bisoxazoline ligands can be prepared as described in Barnes et al., *J. Am. Chem. Soc.*, 124(44):13097-13105 (2002), which is hereby incorporated by reference, and/or in U.S. Pat. No. 6,080,857 to Sibi et al., which is hereby incorporated by reference. The conversion of the α,β-unsaturated imide to the 2-substituted-isoxazolidin-5-one can be carried out, for example, by contacting the α,β-unsaturated imide with the Lewis acid followed by addition of the substituted hydroxyl amine. For example, the Lewis acid and chiral ligand (e.g., chiral bisoxazoline ligand) can be dissolved in a suitable solvent (e.g., methylene chloride or other chlorinated hydrocarbon solvent) and stirred for from about 5 minutes to about 5 hours (e.g., for about 30 minutes) at from about 10° C. to about 40° C. (e.g., at about room temperature). The α,β-unsaturated imide can then be added, and the resulting mixture can be stirred for from about 5 minutes to about 5 hours (e.g., for about 30 minutes) at from about 10° C. to about 40° C. (e.g., at about room temperature). The mixture can then be cooled (e.g., to about −40° C.) and stirring can be continued at this temperature for an additional period of time (e.g., from about 5 minutes to about 5 hours, such as for about 30 minutes). The substituted hydroxyl amine, dissolved in a suitable solvent (e.g., methylene chloride or other chlorinated hydrocarbon solvent) can then be added to the mixture. When complete, the reaction can be quenched using a suitable acid (e.g., trifluoroacetic acid), followed by stirring for from about 5 minutes to about 5 hours (such as for about 30 minutes) at about −40° C. The resulting 2-substituted-isoxazolidin-5-one can then be isolated by conventional techniques (e.g., filtration and/or extraction), and it can be purified, for example, by chromatography. In this procedure, the molar amount of Lewis acid employed can range from about 0.1 to about 1 times (e.g., about 0.3 times) the molar amount of α,β-unsaturated imide to be reacted, and the molar ratio of substituted hydroxyl amine:α,β-unsaturated imide can range from about 0.5 to about 5, such as from about 1 to about 2 and/or about 1.5. Where a chiral ligand is employed, it is generally used in a chiral ligand:Lewis acid molar ratio of from about 0.9 to about 1.1 and/or about 1.

Illustratively, where β-amino acids having Formula I:

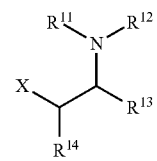

are to be prepared using α,β-unsaturated imides having Formula IV:

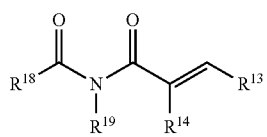

the α,β-unsaturated imide of Formula IV can be converted to a 2-substituted-isoxazolidin-5-one having the formula ("Formula V"):

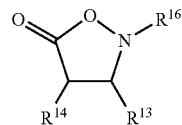

where $R^{16}$ is a substituted or unsubstituted alkyl group or a substituted or unsubstituted aryl group and where $R^{13}$ and $R^{14}$ are as set forth above with regard to Formula IV.

The method of the present invention further includes converting the 2-substituted-isoxazolidin-5-one to the β-amino acid. The conversion can be carried out by hydrogenation, for example, using a suitable hydrogenation catalyst, such as palladium on carbon or zinc. The conversion can be direct, for example, by contacting the 2-substituted-isoxazolidin-5-one with hydrogen gas in the presence of a suitable hydrogenation catalyst. Alternatively, the conversion can be indirect, for example, as in the case where the 2-substituted-isoxazolidin-5-one is first converted to an intermediary compound which is then converted to the β-amino acid by contacting the intermediary compound with hydrogen gas in the presence of a suitable hydrogenation catalyst. For example, a 2-substituted-4-monosubstituted-isoxazolidin-5-one (Formula V, $R^{14} \neq H$) can be first converted to a 2-substituted-4,4-disubstituted-isoxazolidin-5-one, which can then be converted to an α,α-disubstituted-β-amino acid by contacting the 2-substituted-4,4-disubstituted-isoxazolidin-5-one with hydrogen gas in the presence of a suitable hydrogenation catalyst. Irrespective of whether the conversion is direct or indirect, it can be carried out using conventional hydrogenation conditions, such as by dissolving or suspending the material to be hydrogenated in a suitable hydrogenation solvent (e.g., an ether solvent, such as dioxane) and contacting the resulting mixture with hydrogen gas, for example, at ambient pressure and at from about 10° C. to about 100° C. (such as at from about room temperature to about 60° C., at about room temperature, and/or at about 60° C.), for a period of time sufficient to effect the hydrogenation reaction, such as from about 4 hours to about 3 days, from about 12 hours to about 24 hours, and/or for about 16 hours. The resulting β-amino acid can then be separated, for example, by filtration and/or solvent evaporation; and it can then be purified, for example, by chromatography.

The method of the present invention can further include other steps. For example, as discussed briefly above, the method of the present invention can further include converting the 2-substituted-isoxazolidin-5-one (produced from the α,β-unsaturated imide) to another 2-substituted-isoxazolidin-5-one prior to converting the 2-substituted-isoxazolidin-5-one to the β-amino acid by catalytic hydrogenation. Illustratively, as explained above, a 2-substituted-4-monosubstituted-isoxazolidin-5-one (e.g., a compound of Formula V, $R^{14} \neq H$) can be first converted to a 2-substituted-4,4-disubstituted-isoxazolidin-5-one, which can then be converted to an α,α-disubstituted-β-amino acid by contacting the 2-substituted-4,4-disubstituted-isoxazolidin-5-one with hydrogen gas in the presence of a suitable hydrogenation catalyst. More particularly, a compound of Formula V, $R^{14} \neq H$, can be converted to a 2-substituted-4,4-disubstituted-isoxazolidin-5-one having the following formula ("Formula VI"):

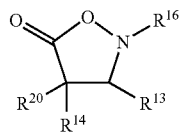

where $R^{13}$ is selected from a hydrogen atom, an alkyl group, an aryl group, and a carboxylic acid group other than COOH; where $R^{14}$ and $R^{20}$ are independently selected from an alkyl group, an aryl group, a hydroxy group, an alkoxy group, other groups having the formula —OP (P representing a hydroxy protecting moiety), a thiol group, an alkylthio group, an arylthio group, an amine group, a carboxylic acid group, a phosphine group, a sulfonic acid group, and a halogen atom; and where $R^{16}$ is a substituted or unsubstituted alkyl group or a substituted or unsubstituted aryl group. For example, such conversion from a 2-substituted-4-monosubstituted-isoxazolidin-5-one to a 2-substituted-4,4-disubstituted-isoxazolidin-5-one can be effected, for example, by contacting the 2-substituted-4-monosubstituted-isoxazolidin-5-one with an alkyl iodide (e.g., a C1-C6 alkyl iodide, allyl iodide, benzyl iodide, etc.) in the presence of a lithium amide base, such as lithium hexamethyldisilazide ("LiHMDS"), at low temperature (e.g., at from about −40° C. to about −90° C., such as at about −78° C.) for from about 30 minutes to about 1 day, such as for from about 1 hour to about 6 hours and/or for about 3 hours. Once the 2-substituted-4,4-disubstituted-isoxazolidin-5-one is formed, it can be converted, e.g., by contacting the 2-substituted-4,4-disubstituted-isoxazolidin-5-one with hydrogen gas in the presence of a suitable hydrogenation catalyst, to an α,α-disubstituted-β-amino acid, such as an α,α-disubstituted-β-amino acid having Formula II:

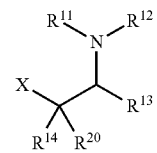

where $R^{11}$ and $R^{12}$ are independently selected from H, an alkyl group, and an aryl group or $R^{11}$ and $R^{12}$, together with the nitrogen atom to which they are bonded, form a ring; where $R^{13}$ is selected from a hydrogen atom, an alkyl group, an aryl group, and a carboxylic acid group other than COOH; where $R^{14}$ and $R^{20}$ are independently selected from an alkyl group, an aryl group, a hydroxy group, an alkoxy group, other groups having the formula —OP (P representing a hydroxy protecting moiety), a thiol group, an alkylthio group, an arylthio group, an amine group, a carboxylic acid group, a phosphine group, a sulfonic acid group, and a halogen atom; and where X is a carboxylic acid group.

Alternatively and as further illustration of the additional steps which the present method can optionally include, where it is desired that the β-amino acid's α position be disubstituted (e.g., where the β-amino acid is of Formula II in which neither $R^{14}$ nor $R^{20}$ is a hydrogen atom), the method can be carried out to produce an α-monosubstituted-β-amino acid (e.g., of Formula I in which $R^{14}$ is not a hydrogen atom), and the α-monosubstituted-β-amino acid (e.g., of Formula I in which $R^{14}$ is not a hydrogen atom) can be converted to the α,α-disubstituted-β-amino acid, for example by replacing the α-monosubstituted-β-amino acid's α hydrogen with the desired substituent using, for example, conventional alkylation protocols, such as those described in Ishikawa et al., *Synlett.*, 1171 (1995); Carruthers, *Some Modern Methods of Organic Synthesis*, 3rd ed., New York: Cambridge University Press (1986); Smith, *Organic Synthesis*, 2nd ed., Boston: McGraw Hill (2002); Smith et al., *Advanced Organic Chemistry*, 5th ed., New York: J. Wiley Interscience (2001); Tietze et al., *Reactions and Synthesis in the Organic Chemistry Laboratory*, Mill Valley, Calif.: University Science Books (1989); Larock, *Comprehensive Organic Transformations*, 2nd ed., New York: Wiley VCH, (1999); Morrison et al., *Organic Chemistry*, 3rd ed., Boston: Allyn and Bacon, Inc. (1973); Kemp et al., *Organic Chemistry*, New York, Worth Publishers Inc. (1980); and House, *Modern Synthetic Reac-* tions, Menlo Park, Calif.: The Benjamin/Cummings Publishing Company (1972), which are hereby incorporated by reference. Thus, for example, the step of converting a 2-substituted-isoxazolidin-5-one of Formula V to a β-amino acid of Formula II in which $R^{14}$ and $R^{20}$ are not hydrogen atoms can be carried out by converting the 2-substituted-isoxazolidin-5-one of Formula V to a β-amino acid of Formula I in which $R^{14}$ is not a hydrogen atom and then converting this β-amino acid to the β-amino acid of Formula II in which $R^{20}$ is not a hydrogen atom.

As still further illustration, where it is desired that the carboxylic acid function (e.g., the X substituent in Figure I) be an ester function, the method of the present invention can be carried out to produce a β-amino acid of Formula I in which X is a COOH group. The COOH group can then be reacted, for example, with an alcohol to produce the desired ester. Thus, for example, the step of converting a 2-substituted-isoxazolidin-5-one (e.g., of Formula V) to a β-amino acid (e.g., of Formula I in which X is a functional group other than COOH) can be carried out by converting (e.g., by hydrogenation) the 2-substituted-isoxazolidin-5-one to a β-amino acid bearing a free carboxylic acid group (e.g., a β-amino acid of Formula I in which X is COOH) and then converting the β-amino acid bearing a free carboxylic acid group (e.g., of Formula I in which X is COOH) to the β-amino acid of Formula I in which X is a functional group other than COOH. To effect the latter conversions (e.g., from X=COOH to X=COOR; from X=COOH to X=COOH; from X=COOH to X=COOH'; from X=COOH to X=COOH; from X=COOH to X=COSR; from X=COOH to X=CHO; from X=COOH to X=COR, etc., where M is a cation, such as a metal cation, and R and R' are independently selected from, for example, alkyl and aryl), any conventional method can be employed, such as those described, for example, in Carruthers, *Some Modern Methods of Organic Synthesis*, 3rd ed., New York: Cambridge University Press (1986); Smith, *Organic Synthesis*, 2nd ed., Boston: McGraw Hill (2002); Smith et al., *Advanced Organic Chemistry*, 5th ed., New York: J. Wiley Interscience (2001); Tietze et al., *Reactions and Synthesis in the Organic Chemistry Laboratory*, Mill Valley, Calif.: University Science Books (1989); Larock, *Comprehensive Organic Transformations*, 2nd ed., New York: Wiley VCH, (1999); Morrison et al., *Organic Chemistry*, 3rd ed., Boston: Allyn and Bacon, Inc. (1973); Kemp et al., *Organic Chemistry*, New York, Worth Publishers Inc. (1980); and House, *Modern Synthetic Reactions*, Menlo Park, Calif.: The Benjamin/Cummings Publishing Company (1972), which are hereby incorporated by reference.

As still further illustration, where it is desired that the amine group be substituted (e.g., a β-amino acid of Formula I in which $R^{11}$ and/or $R^{12}$ is not a hydrogen atom), the method can be carried out to produce a β-amino acid bearing an unsubstituted amine (e.g., of Formula I in which $R^{11}$ and $R^{12}$ are hydrogen atoms), and the amine hydrogen atom or atoms can then be replaced with the desired substituent. Thus, for example, the step of converting a 2-substituted-isoxazolidin-5-one of Formula V to a β-amino acid of Formula I in which $R^{11}$ and/or $R^{12}$ are not hydrogen atoms can be carried out by converting the 2-substituted-isoxazolidin-5-one of Formula V to a β-amino acid of Formula I in which $R^{11}$ and $R^{12}$ are hydrogen atoms and then converting the β-amino acid of Formula I in which $R^{11}$ and $R^{12}$ are hydrogen atoms to the β-amino acid of Formula I in which at least one of $R^{11}$ and $R^{12}$ is not a hydrogen atom. To effect the latter conversions (e.g., from $R^{11}$=H to $R^{11}$=alkyl; from $R^{11}$=H to $R^{11}$=aryl; from $R^{11}$=H to $R^{11}$=COR; from $R^{11}$=H to $R^{11}$=COOR; from $R^{11}$=$R^{12}$=H to $R^{11}$=$R^{12}$=alkyl; from $R^{11}$=$R^{12}$=H to $R^{11}$=$R^{12}$=aryl; from $R^{11}$=$R^{12}$=H to $R^{11}$=alkyl, $R^{12}$=aryl; from $R^{11}$=$R^{12}$=H to $R^{11}$=alkoxycarbonyl, $R^{12}$=alkyl; etc., where R is, for example, alkyl or aryl), any conventional method can be employed, such as those described, for example, in Carruthers, *Some Modern Methods of Organic Synthesis*, 3rd ed., New York: Cambridge University Press (1986); Smith, *Organic Synthesis*, 2nd ed., Boston: McGraw Hill (2002); Smith et al., *Advanced Organic Chemistry*, 5th ed., New York: J. Wiley Interscience (2001); Tietze et al., *Reactions and Synthesis in the Organic Chemistry Laboratory*, Mill Valley, Calif.: University Science Books (1989); Larock, *Comprehensive Organic Transformations*, 2nd ed., New York: Wiley VCH, (1999); Morrison et al., *Organic Chemistry*, 3rd ed., Boston: Allyn and Bacon, Inc. (1973); Kemp et al., *Organic Chemistry*, New York, Worth Publishers Inc. (1980); and House, *Modern Synthetic Reactions*, Menlo Park, Calif.: The Benjamin/Cummings Publishing Company (1972), which are hereby incorporated by reference.

As one skilled in the art will note, many of the compounds depicted herein by structural formulae contain chiral centers. Where the geometry of such a chiral center is not specified, the structural formula is meant to include compounds in which the chiral center is in the R-configuration, compounds in which the chiral center is in the S-configuration, as well as mixtures (e.g., racemic mixtures) of such compounds.

As one skilled in the art will appreciate, while the amine functions depicted in the formulae set forth herein are shown as being in the free base form, such need not be the case, and these formulae are meant to include structures in which the amine function is present in another form, such as a salt or adduct. Moreover, it will be appreciated that certain β-amino acids described herein (e.g., those in which the carboxylate function is present as a free carboxylic acid group) can exist in an ionic or charge-separated form (where the carboxylate function is deprotonated and the amine function is protonated) or in a neutral form (where the hydrogen remains on the carboxylic acid group). Although the β-amino acids shown in the structural formulae (e.g., Formula I and Formula II) set forth herein depict a neutral form, it is to be understood that these structural formulae are meant to include β-amino acids in the ionic or charge-separated form, β-amino acids in the neutral form, and mixtures (e.g., equilibrium mixtures) thereof. Moreover, the β-amino acids shown in the structural formulae set forth herein are meant to include salts, solvates, and adducts of such β-amino acids.

The present invention, in another aspect thereof, relates to a method for making β-amino acids that are substituted in the α position, that are unsubstituted in the β position, and/or that bear an aryl substituent in the β position. Generally, the method includes providing an appropriate α,β-unsaturated imide, and converting the α,β-unsaturated imide to a β-amino acid, for example, by using a Lewis acid catalyst and hydrogenation. Illustratively, the α,β-unsaturated imide can be cyclized using a Lewis acid catalyst to produce a 2-substituted-isoxazolidin-5-one, which 2-substituted-isoxazolidin-5-one can then be converted, for example, by catalytic hydrogenation or another form of hydrogenation, to the β-amino acid. Alternatively, the α,β-unsaturated imide can be reacted with a Lewis acid catalyst and a substituted hydroxyl amine to produce a non-cyclized intermediate (e.g., as shown hereinbelow in Table 4 of Example 5), which non-cyclized intermediate can then be converted, for example, by catalytic hydrogenation or another form of hydrogenation, to the β-amino acid.

For example, suitable α,β-unsaturated imides which can be used in the method of the present invention to produce β-amino acids of Formula I include those having Formula IV:

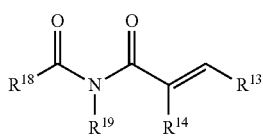

where $R^{13}$ and $R^{14}$ in Formula IV have the same meanings as described above with regard to Formula I; $R^{18}$ can be a substituted or unsubstituted alkyl group (e.g., a substituted or unsubstituted C1-C4 linear alkyl or other linear alkyl, a substituted or unsubstituted branched alkyl, or a substituted or unsubstituted cyclic alkyl), a substituted or unsubstituted aryl group (e.g., a substituted or unsubstituted phenyl group), or an alkoxy group; $R^{19}$ can be a hydrogen atom, a substituted or unsubstituted alkyl group (e.g., a substituted or unsubstituted C1-C4 alkyl), or a substituted or unsubstituted aryl group (e.g., a substituted or unsubstituted phenyl group); or $R^{18}$ and $R^{19}$, together with the atoms to which they are bonded, can form a ring (e.g., a 5-7 membered homocyclic or heterocyclic ring). In one illustrative embodiment, the α,β-unsaturated imide is an α,β-unsaturated imide having Formula IV in which $R^{19}$ is H.

Choice of a particular α,β-unsaturated imide will depend, generally, on the desired α,β substitution pattern in the target β-amino acid product. Illustratively, where an α-substituted-β-amino acid is to be prepared, suitable α,β-unsaturated imides include α-substituted-α,β-unsaturated imides. Similarly, where a β-unsubstituted-β-amino acid is to be prepared, suitable α,β-unsaturated imides include β-unsubstituted-α,β-unsaturated imides; and, where a βaryl-β-amino acid is to be prepared, suitable α,β-unsaturated imides include β-aryl-α, β-unsaturated imides.

As indicated above, the α,β-unsaturated imide can be cyclized using a Lewis acid catalyst to produce a 2-substituted-isoxazolidin-5-one, and the 2-substituted-isoxazolidin-5-one can then be converted, for example, by catalytic hydrogenation, to a β-amino acid. Cyclization of the α,β-unsaturated imide can be carried out using any suitable Lewis acid, such the ones described hereinabove. The cyclization reaction is typically carried out in the presence of a hydroxyl amine, such as a benzyl hydroxyl amine or other hydroxyl amine as described above. The cyclization reaction can be carried out at any suitable temperature (e.g., at or below room temperature, such as at from about 0° C. to about –80° C., at from about –30° C. to about –50° C., and/or at about –40° C.), and for any suitable period of time sufficient to permit the reaction to take place (e.g., from about 1 hour to about 24 hours, such as from about 12 hours to about 20 hours, and/or for about 16 hours). Conversion of the 2-substituted-isoxazolidin-5-one to the β-amino acid can be carried out by catalytic hydrogenation, for example, as described hereinabove.

The present invention, in yet another aspect thereof, relates to a method for making a β-amino acid that is unsubstituted in the β position; that is substituted in the β position with an aryl group; that is substituted in the α position with an aryl group; that bears two substituents in the α position; and/or that is substituted in the α and β positions with groups which, together with the carbon atoms at the α and β positions, form a ring. Generally, the method includes providing an appropriate 2-substituted-isoxazolidin-5-one, and converting the 2-substituted-isoxazolidin-5-one to a β-amino acid, for example, by catalytic hydrogenation or another form of hydrogenation, for example as described hereinabove.

Choice of a particular 2-substituted-isoxazolidin-5-one will depend, generally, on the desired α,β substitution pattern in the target β-amino acid product. Illustratively, where a β-unsubstituted-β-amino acid is to be prepared, suitable 2-substituted-isoxazolidin-5-ones include 2-substituted-3-unsubstituted-isoxazolidin-5-ones; where a β-aryl-β-amino acid is to be prepared, suitable 2-substituted-isoxazolidin-5-ones include 2-substituted-3-aryl-isoxazolidin-5-ones; where an α-aryl-β-amino acid is to be prepared, suitable 2-substituted-isoxazolidin-5-ones include 2-substituted-4-aryl-isoxazolidin-5-ones; and, where an α,α-disubstituted-β-amino acid is to be prepared, suitable 2-substituted-isoxazolidin-5-ones include 2-substituted-4,4-disubstituted-isoxazolidin-5-ones. Similarly, β-amino acids that are substituted in the α and β positions with groups which, together with the carbon atoms at the α and β positions, form a ring can be prepared from 2-substituted-isoxazolidin-5-ones which are substituted in the 3 and 4 positions with groups which, together with the carbon atoms at the 3 and 4 positions, form a ring.

The present invention also relates to a method for making a 2-substituted-isoxazolidin-5-one. The method includes providing an α,β-unsaturated imide and cyclizing the α,β-unsaturated imide under conditions effective to produce the 2-substituted-isoxazolidin-5-one, for example, by contacting the α,β-unsaturated imide with a Lewis acid catalyst (e.g., a chiral Lewis acid catalyst) in the presence of an benzyl hydroxyl amine or another hydroxyl amine.

The present invention, in another aspect thereof, relates to 2-substituted-isoxazolidin-5-ones that are unsubstituted in the 3 position; that are substituted in the 3 position with an aryl group; that are substituted in the 4 position with a non-methyl substituent, such as a substituted or unsubstituted aryl group, a substituted methyl group (e.g., a benzyl group or a chloromethyl group), a substituted or unsubstituted C2-C3 linear alkyl group, a substituted or unsubstituted C4-C6 linear alkyl group, a substituted or unsubstituted branched alkyl group, or a substituted or unsubstituted cyclic alkyl group; that are 4,4-disubstituted; and/or that are substituted in the 3 and 4 positions with groups which, together with the carbon atoms at the 3 and 4 positions, form a ring.

In another aspect, the present invention relates to α,β-unsaturated imides that are substituted in the α position, for example, with an alkyl group, an aryl group, a hydroxy group, an alkoxy group (which is meant to include aryloxy groups (e.g., phenoxy groups)), other groups having the formula —OP (where P is a hydroxy protecting moiety, such as where —OP represents O—COR, O—SiR$_3$, etc., where each R independently represents a substituted or unsubstituted alkyl or aryl group), a thiol group, an alkylthio group, an arylthio group, an amine group (which is meant to include unsubstituted, monosubstituted, and disubstituted (e.g., with aryl or alkyl groups) amine groups), a carboxylic acid group (which is meant to include COOH groups as well as carboxylic acid derivatives, e.g., carboxylic acid esters, amides, etc.), a phosphine group, a sulfonic acid group, a halogen atom (e.g., F, Cl, Br, and I), and the like. Such α,β-unsaturated imides that are substituted in the α position are meant to also include α,β-unsaturated imides that are substituted in the α and β positions with groups which, together with the carbon atoms at the α and β positions, form a ring.

The present invention is further illustrated with the following examples.

EXAMPLES

Example 1

Synthesis β-Amino Acids and Intermediates Useful in Such Synthesis

Example 1, along with the following Example 2, reports a chiral Lewis acid-mediated conjugate amine addition protocol for the synthesis of a variety of α,β-disubstituted-β-amino acids (more particularly, α-monosubstituted-βmonosubstituted-β-amino acids) with high diastereo- and enantio-selectivity. The protocol is summarized in Scheme I.

SCHEME I

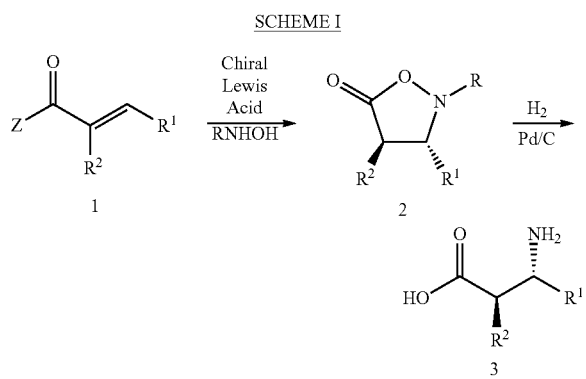

Optimizing the reaction of 1→3 involves rotamer control in the substrate. It is believed that traditional templates, such as oxazolidinones, experience poor reactivity due to problematic $A^{1,3}$ interactions in either rotamer. Such $A^{1,3}$ interactions are illustrated in 4 and 5 in Scheme II (Sibi et al., *J. Am. Chem. Soc.*, 124:984ff (2002), which is hereby incorporated by reference).

SCHEME II

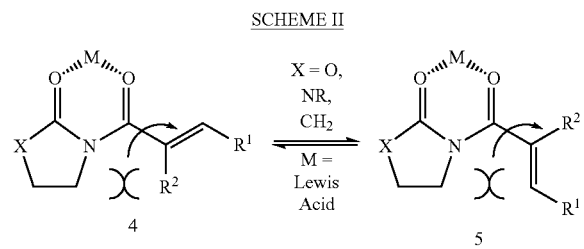

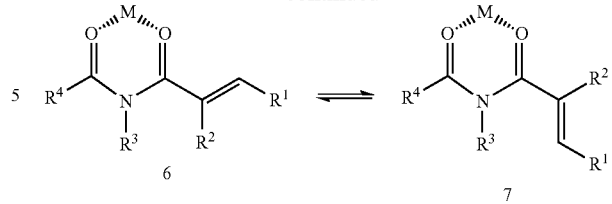

It is believed that, to relieve strain, the C—C bond of the enoates twists, breaking conjugation which results in diminished reactivity at the βcarbon. Our hypothesis was that the use of imides with an N—H group (e.g., 6 in Scheme II, $R^3$=H, a template described in Myers et al., *J. Am. Chem. Soc.*, 121:8959ff (1999) and Sibi et al., *J. Am. Chem. Soc.*, 124:984ff (2002), which are hereby incorporated by reference) would eliminate the $A^{1,3}$ strain present in 4 and 5 and, thus, would allow for planar enoates with normal reactivity. We also thought that s-cis/s-trans rotamer control between 6 and 7 would remain possible and that tunable reactivity should be available (e.g., $R^4$=alkyl, aryl). Literature reports (Goodman et al., *Adv. Synth. Catal.*, 344:953ff (2002), which is hereby incorporated by reference) and our own work (Luesch et al., *J. Nat. Prod.*, 65:996ff (2002); Pettit et al., *Heterocycles*, 28:553ff (1989), and Mynderse et al., *J. Nat. Prod.*, 51:1299 (1988), which are hereby incorporated by reference) have shown that N-benzyl hydroxyl amine adds to enoates in a concerted fashion. We surmised that rotamer control for the substrate 1 combined with concerted addition of N-benzyl hydroxyl amine in the presence of a chiral Lewis acid should provide access to 2 with good relative as well as absolute stereocontrol.

Our experiments began with addition of N-benzyl hydroxyl amine to tiglates (8-17) with different achiral templates using catalytic amounts (5-30 mol %) of a chiral Lewis acid derived from ligand 18 and magnesium salts, as shown in Table 1. That the same isoxazolidinone product formed regardless of template streamlined our assessment of enantioselectivity. Results from these studies are also shown in Table 1.

TABLE 1

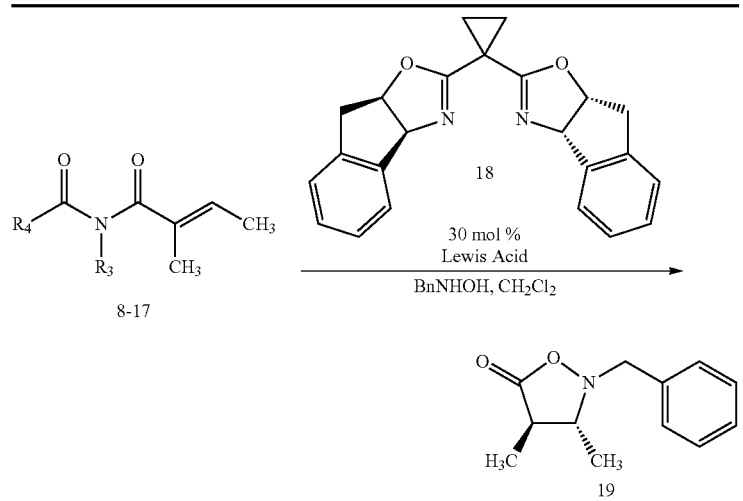

| Entry | SM[a] | R[3] | R[4] | Lewis Acid | T ° C. | Yield[b] | de[c] | ee[d] |
|---|---|---|---|---|---|---|---|---|
| 1 | 8 |  | —CH$_2$CH$_2$CH$_2$— | Mg(ClO$_4$)$_2$ | −40 | 10 | 95 | 70 |
| 2 | 9 |  | —CH$_2$CH$_2$O— | Mg(ClO$_4$)$_2$ | −40 | 8 | 95 | 40 |
| 3 | 10 | Me | Ph | Mg(ClO$_4$)$_2$ | −40 | 10 | 60 | 18 |
| 4 | 11 | H | Ph | Mg(ClO$_4$)$_2$ | −40 | 47 | 94 | 75 |

TABLE 1-continued

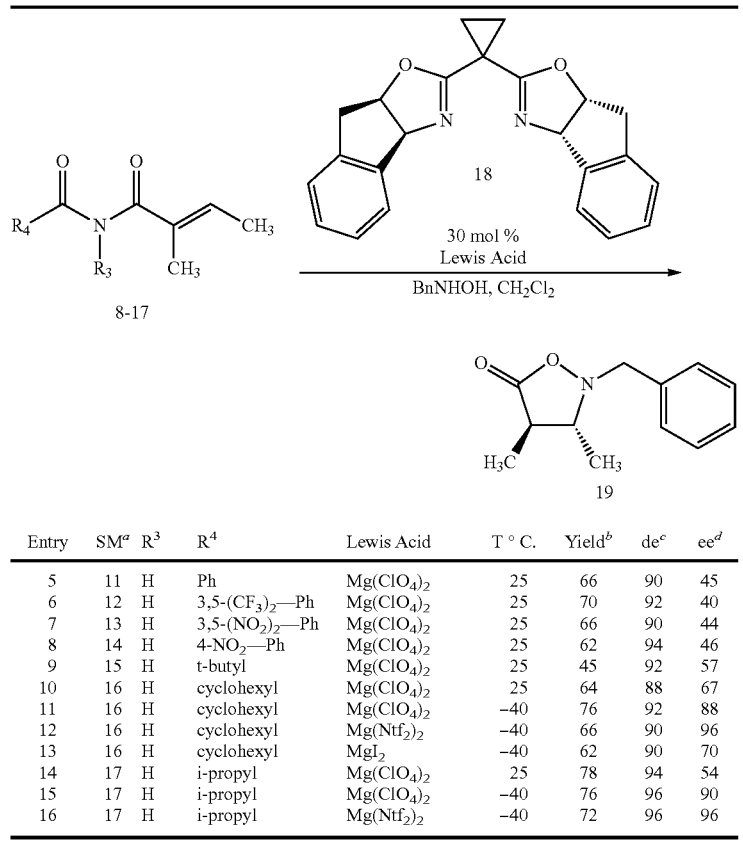

| Entry | SM[a] | R[3] | R[4] | Lewis Acid | T °C. | Yield[b] | de[c] | ee[d] |
|---|---|---|---|---|---|---|---|---|
| 5 | 11 | H | Ph | Mg(ClO$_4$)$_2$ | 25 | 66 | 90 | 45 |
| 6 | 12 | H | 3,5-(CF$_3$)$_2$—Ph | Mg(ClO$_4$)$_2$ | 25 | 70 | 92 | 40 |
| 7 | 13 | H | 3,5-(NO$_2$)$_2$—Ph | Mg(ClO$_4$)$_2$ | 25 | 66 | 90 | 44 |
| 8 | 14 | H | 4-NO$_2$—Ph | Mg(ClO$_4$)$_2$ | 25 | 62 | 94 | 46 |
| 9 | 15 | H | t-butyl | Mg(ClO$_4$)$_2$ | 25 | 45 | 92 | 57 |
| 10 | 16 | H | cyclohexyl | Mg(ClO$_4$)$_2$ | 25 | 64 | 88 | 67 |
| 11 | 16 | H | cyclohexyl | Mg(ClO$_4$)$_2$ | −40 | 76 | 92 | 88 |
| 12 | 16 | H | cyclohexyl | Mg(Ntf$_2$)$_2$ | −40 | 66 | 90 | 96 |
| 13 | 16 | H | cyclohexyl | MgI$_2$ | −40 | 62 | 90 | 70 |
| 14 | 17 | H | i-propyl | Mg(ClO$_4$)$_2$ | 25 | 78 | 94 | 54 |
| 15 | 17 | H | i-propyl | Mg(ClO$_4$)$_2$ | −40 | 76 | 96 | 90 |
| 16 | 17 | H | i-propyl | Mg(Ntf$_2$)$_2$ | −40 | 72 | 96 | 96 |

[a]SM = starting material
[b]isolated yield after column chromatography
[c]diastereomeric excess determined by $^1$H-NMR (500 MHz)
[d]determined by chiral HPLC Conjugate amine addition to pyrrolidinone (8) or oxazolidinone (9) derived tiglate gave low yields, although the diastereoselectivity and enantioselectivity were good (entries 1 and 2 in Table 1). With regard to diastereoselectivity, the major diastereomer of 18 had trans stereochemistry for the substituents as established by NMR. This is believed to be a consequence of the syn addition of the amine to the substrate in a concerted manner. Reaction with tertiary imide 10 (R$^3$=CH$_3$) was also very slow and low-yielding, and this reaction gave 19 with low selectivity (entry 3 in Table 1). By contrast, secondary imides 11-17 (R$^3$=H), lacking the A$^{1,3}$ strain present in 8-10, were much more reactive and gave good yields. Our initial attempt with benzimide 11 (entry 4 in Table 1) gave excellent diastereoselectivity and good enantioselectivity, suggesting that even with R$^3$=H, s-cis/s-trans rotamer control is satisfactory. Increasing the reaction temperature led to higher yield for 19 with a concomitant decrease in enantioselectivity (entry 5 in Table 1). In entries 6-8, electron withdrawing groups were found to enhance reactivity (reaction time: 1 h for 13 and 8 h for 11 at room temperature) with little impact on selectivity. Reactions with imides containing alkyl R$^4$ substituents (15-17) gave higher selectivity as compared to aryl groups (entries 9, 10, and 14 in Table 1). When the magnesium counterion was varied (entries 11-13, 15-16 in Table 1), magnesium triflimide gave optimal enantio-selectivity. When temperature, imide R$^4$, and chiral Lewis acid were all optimized (entries 9-16 in Table 1), the optimal substrate was determined to be 17, which gave 19 with outstanding levels of selectivity (96% ee and 96% de), as shown by entry 16 in Table 1, when magnesium triflimide was used as a Lewis acid. These results clearly demonstrate that a highly enantioselective method for the synthesis of α,β-disubstituted-β-amino acids (more particularly, α-monosubstituted-β-monosubstituted-β-amino acids) is at hand.

The results from breadth and scope studies for the preparation of a variety of isoxazolidinones (19, 31-41) using 5 mol % of the catalyst and isopropyl substituted imides are shown in Table 2.

TABLE 2

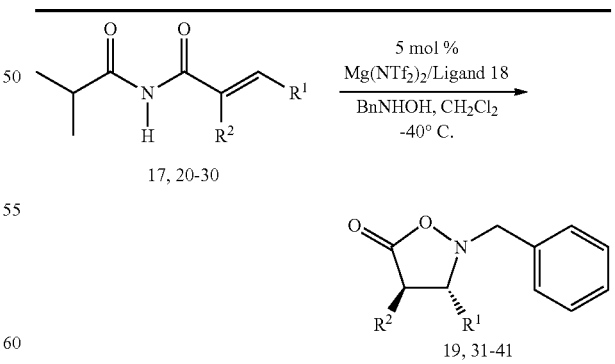

| Entry | Starting Material | R$^1$ | R$^2$ | Product | Yield[a] | de[b] | ee[c] |
|---|---|---|---|---|---|---|---|
| 1 | 17 | methyl | methyl | 19 | 72 | 96 | 96 |
| 2 | 20 | methyl | ethyl | 31 | 70 | 98 | 86 |
| 3 | 21 | methyl | bromo | 32 | 76 | 99 | 76 |

TABLE 2-continued

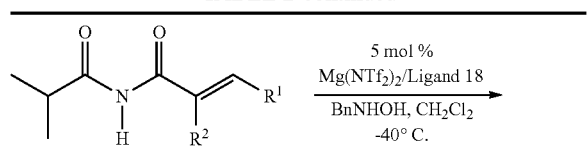

17, 20-30

19, 31-41

| Entry | Starting Material | R[1] | R[2] | Product | Yield[a] | de[b] | ee[c] |
|---|---|---|---|---|---|---|---|
| 4 | 22 | methyl | phenyl | 33 | 90 | 95 | 90 |
| 5 | 23 | ethyl | methyl | 34 | 82 | 96 | 90 |
| 6 | 24 | n-propyl | methyl | 35 | 92 | 95 | 89 |
| 7[d] | 25 | i-propyl | methyl | 36 | 28 | 95 | 81 |
| 8[e] | 26 | i-butyl | methyl | 37 | 64 | 95 | 77 |
| 9 | 27 | n-heptyl | methyl | 38 | 73 | 96 | 85 |
| 10 | 28 | ethyl | ethyl | 39 | 72 | 96 | 60 |
| 11[d] | 29 | phenyl | methyl | 40 | 38 | 95 | 76 |
| 12[d] | 30 | phenyl | phenyl | 41 | 49 | 93 | 84 |

[a]isolated yield after chromatography
[b]diastereomeric excess determined by $^1$H-NMR (500 MHz)
[c]determined by chiral HPLC
[d]reactions at 0° C. using 30 mol % of catalyst
[e]10 mol % of catalyst As illustrated earlier, amine addition to the tiglate 17 gave 19 with 96% ee (entry 1 in Table 2). Reaction with a bulkier α-ethyl group was equally effective (entry 2 in Table 2). A bromo substituent (entry 3 in Table 2) as well as a phenyl substituent (entry 4 in Table 2) at the α position are also well tolerated in the reaction leading to products 32 and 33, respectively, with good yield and high selectivity. Reactions with several substrates with changes in the βsubstituent were examined next (entries 5-9 in Table 2). All of these gave isoxazolidinones with high selectivity. The chemical efficiency with the bulky β-isopropyl group (25) was low (entry 7 in Table 2). Amine addition to 28, containing α,β-diethyl groups, gave 39 in good yield. However the enantioselectivity was modest (entry 10 in Table 2). Reactions with a β-phenyl substituent were also examined (entries 11 and 12 in Table 2). These are relatively unreactive substrates, and reactions were carried out at 0° C. to get modest yields. However, the enantioselectivity for 40 and 41 remained good. The results from these studies demonstrate that a variety of substituted isoxazolidinones can be prepared with high diastereo- and enantioselectivity.

The product isoxazolidinones can be easily converted to the corresponding amino acids by a simple hydrogenation, as shown in Scheme III.

SCHEME III

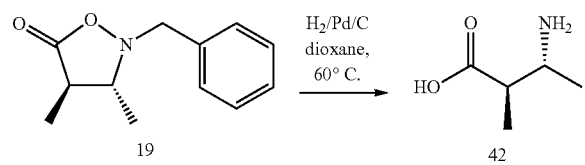

Catalytic hydrogenation of 19 using Pd/C on a 5 g scale gave (2R,3R)-3-amino-2-methyl-butanoic acid (α-methyl-β-methyl-β-amino acid) in 90% yield. Compounds 31, 36, 37, and 40 were also converted to the corresponding amino acids by hydrogenation. Thus, α,β-disubstituted-β-amino acids (more particularly, α-monosubstituted-β-monosubstituted-β-amino acids) can be synthesized in four steps from the unsaturated acids in good overall yields and high enantiopurity using chiral catalysis.

As discussed in more detain in Example 11 hereinbelow, we have a tentative model for the observed stereochemistry based on the identity of 41 as well as our previous work on amine additions using magnesium salts and ligand 18.

In conclusion, this example illustrates a novel and practical chiral catalytic method for the synthesis of α,β-disubstituted-β-amino acids (more particularly, α-monosubstituted-β-monosubstituted-β-amino acids) in good overall yields and enantioselectivity. The availability of highly enantioenriched isoxazolidinones provides access to syn disubstituted as well as α,α,β-trisubstituted compounds by base-mediated inversion or alkylation protocols, for example, as discussed in Examples 8 and 9, hereinbelow, and in Ishikawa et al., Synlett., 1171ff (1995), which is hereby incorporated by reference.

Detailed preparative protocols for the synthesis of imides 8-17 and 20-30, the conversion of imides 8-17 and 20-30 to isoxazolidin-5-ones 19 and 31-41, and the conversion of isoxazolidin-5-ones to β-amino acids are provided in Example 2 and in Sibi et al., "Enantioselective Synthesis of α,βDisubstituted-β-Amino Acids," J. Am. Chem. Soc., 125(39):11796-11797 (2004) and the supporting information associated therewith, which are hereby incorporated by reference).

Example 2

Detailed Protocols for the Synthesis of Imides and Isoxazolidin-5-ones and Their Conversion into β-Amino Acids General Experimental. Dichloromethane was distilled from calcium hydride prior to use. Magnesium perchlorate and magnesium triflimide were purchased from Aldrich chemicals. N-benzyl hydroxyl amine was obtained from commercial sources, and cyclopropyl bis oxazoline ligand 3aS-[2(3'aR,8'aS),3aa,8aa]}-2,2'-(cyclopropyl-idene)-bis{3a,8α-dihydro-8H-indeno[1,2-d]-oxazole was prepared using the procedures described in Sibi et al., J. Org. Chem., 62:3800ff (1997), which is hereby incorporated by reference. Flash chromatography was performed using EM Science silica gel 60(230-400 mesh). All glassware was oven dried, assembled hot, and cooled under a stream of nitrogen before use. Reactions with air sensitive materials were carried out by standard syringe techniques.

$^1$H-NMR were recorded on a Varian Unity/Inova-500 NB (500 MHz) or a Varian Unity/Inova-400 NB (400 MHz) spectrometers. Chemical shifts are reported in parts per million (ppm) down field from TMS, using residual CDCl$_3$ (7.27 ppm) as an internal standard. Data are reported as follows: Chemical shift, multiplicity (s=singlet, d=doublet, t=triplet,

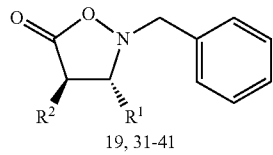

q=quartet, dd=doublet of a doublet, m=multiplet, br=broad), coupling constants, and integration. $^{13}$C-NMR was recorded in a Varian Unity/Inova-500 NB (125 MHz) or Varian Unity/Inova-400 NB (100 MHz) spectrometers, using broadband proton decoupling. Chemical shifts are reported in parts per million (ppm) downfield from TMS, using the middle resonance of CDCl$_3$ (77.0 ppm) as an internal standard. HPLC analyses were carried out on a Waters 515 HPLC pump and a 2487 dual λ absorbance detector connected to a PC with Millennium workstation. Rotations were recorded on a JASCO-DIP-370 instrument. High Resolution Mass Spectra (HRMS) (EI+) were obtained from Mass Spectrometry Laboratory, Ohio State University, Columbus, Ohio.

General Procedure for the Synthesis of Imides. Under nitrogen, 30 mmol of tiglic acid or the respective acid was dissolved in 3.0 mL of dry dichloromethane, followed by addition of 32 mmol of oxalyl chloride and a drop of DMF. After 2 hours, the volatile impurities were evacuated, and tigloyl chloride or the respective acid chloride was obtained. In a separate flask, 30 mmol of carboxamide was dissolved in 120 mL of dry THF. This was followed by the addition of NaH (75 mmol of 60%) (or equimolar amounts of n-BuLi for pyrrolidinone and oxazolidinone) at 0° C. After stirring the reaction for 30 minutes, tigloyl chloride or the respective chloride was added at room temperature, and the reaction was stirred for 2 hours. After completion of the reaction, it was quenched by the addition of 30 mL of 1N HCl. The reaction mixture was extracted with dichloromethane (3×30 mL). The organic layer was washed with saturated sodium bicarbonate, dried over MgSO$_4$, and purified by flash chromatography using silica gel (10% ethyl acetate:hexane) to yield 60-80% of the imide.

1-(1-Oxo-2-methyl-2-butenyl)-2-pyrrolidinone (8): $^1$H-NMR (CDCl$_3$, 500 MHz): δ 1.75 (d, J=7.0 Hz, 3H), 1.83 (s, 3H), 2.04 (m, 2H), 2.54 (t, J=7.5 Hz, 2H), 3.77 (t, J=7.5 Hz, 2H), 6.08 (q, J=7.0 Hz, 1H). $^{13}$C-NMR (CDCl$_3$, 125 MHz): δ 13.5, 14.1, 17.9, 33.5, 46.4, 133.2, 133.4, 172.9, 174.7. HRMS calcd. for C$_9$H$_{13}$NO$_2$Na$^+$ is 190.0838 and observed=190.0835.

3-(1-Oxo-2-methyl-2-butenyl)-2-oxazolidinone (9): $^1$H-NMR (CDCl$_3$, 500 MHz): δ 1.70 (d, J=7.0 Hz, 3H), 1.73 (s, 3H), 4.05 (t, J=5.0 Hz, 2H), 4.36 (t, J=5.0 Hz, 2H), 5.84 (q, J=7.0 Hz, 1H). $^{13}$C-NMR (CDCl$_3$, 125 MHz): δ 13.3, 13.8, 44.2, 62.8, 131.4, 137.9, 167.9, 176.2.

N-methyl-N-benzoyl-2-methyl-2-butenimide (10): $^1$H-NMR (CDCl$_3$, 400 MHz): δ 1.40 (d, J=7.0 Hz, 3H), 1.44 (s, 3H), 3.37 (s, 3H), 5.91 (q, J=7.0 Hz, 1H), 7.36 (m, 5H). $^{13}$CNMR (CDCl$_3$, 100 MHz): δ 13.0, 13.8, 33.4, 127.9, 128.8, 131.5, 135.3, 136.4, 138.2, 174.5, 176.5. HRMS calcd. for C$_{13}$H$_{15}$NO$_2$Na$^+$ is 240.0995 and observed=240.1003.

N-benzoyl-2-methyl-2-butenimide (11): $^1$H-NMR (CDCl$_3$, 400 MHz): δ 1.75 (d, J=6.8 Hz, 3H), 1.78 (s, 3H), 6.61 (q, J=6.8 Hz, 1H), 7.56 (m, 5H), 8.73 (br s, 1H). $^{13}$CNMR (CDCl$_3$, 100 MHz): δ 12.8, 14.8, 129.0, 133.4, 134.4, 134.8, 138.0, 140.0, 173.4, 174.9. HRMS calcd. for C$_{12}$H$_{13}$NO$_2$Na$^+$ is 226.0838 and observed=226.0827.

N-(3,5-bis trifluoro methyl)-benzoyl-2-methyl-2-butenimide (12): $^1$H-NMR (CDCl$_3$, 400 MHz): δ 1.89 (d, J=7.0 Hz, 3H), 1.91 (s, 3H), 6.67 (q, J=7.0 Hz, 1H), 8.04 (s, 1H), 8.17 (s, 2H), 8.89 (br s, 1H). $^{13}$C-NMR (CDCl$_3$, 100 MHz): δ 12.5, 14.8, 121.6, 124.3, 126.0, 128.7, 132.1 (q, J=29.5 Hz), 136.1, 136.8, 166.6, 168.3. HRMS calcd. for C$_{14}$H$_{11}$F$_6$NO$_2$Na$^+$ is 362.0586 and observed=362.0586.

N-(3,5-dinitro)-benzoyl-2-methyl-2-butenimide (13): $^1$H-NMR (CDCl$_3$, 400 MHz): δ 1.87 (d, J=6.4 Hz, 3H), 1.90 (s, 3H), 6.75 (q, J=6.4 Hz, 1H), 8.63 (s, 1H), 8.77 (s, 1H), 9.17 (s, 2H). $^{13}$C-NMR (CDCl$_3$, 100 MHz): δ 12.4, 15.0, 121.6, 122.9, 128.7, 130.1, 137.9, 148.5, 166.6, 167.4. HRMS calcd. for C$_{12}$H$_{11}$N$_3$O$_6$Na$^+$ is 316.0540 and observed=316.0520.

N-(4-nitro)-benzoyl-2-methyl-2-butenimide (14): $^1$H-NMR (CDCl$_3$, 400 MHz): δ 1.85 (d, J=6.8 Hz, 3H), 1.89 (s, 3H), 6.66 (q, J=6.8 Hz, 1H), 7.86 (d, J=8.0 Hz, 2H), 8.28 (d, J=8.0 Hz, 2H), 8.65 (br s, 1H). $^{13}$C-NMR (CDCl$_3$, 100 MHz): δ 12.5, 14.8, 123.9, 129.3, 132.2, 136.6, 139.7, 150.1, 167.3, 167.9. HRMS calcd. for C$_{12}$H$_{12}$N$_2$O$_4$Na$^+$ is 271.0690 and observed=271.0701.

N-t-butyl carboxy-2-methyl-2-butenimide (15): $^1$H-NMR (CDCl$_3$, 400 MHz): δ 1.18 (s, 9H), 1.74 (d, J=6.4 Hz, 3H), 1.84 (s, 3H), 6.42 (q, J=6.4 Hz, 1H), 8.38 (br s, 1H). $^{13}$C-NMR (CDCl$_3$, 100 MHz): δ 12.6, 14.4, 27.3, 40.6, 133.3, 133.8, 168.1, 176.0. HRMS calcd. for C$_{10}$H$_{17}$NO$_2$Na$^+$ is 206.1151 and observed=206.1169.

N-cyclohexyl carboxy-2-methyl-2-butenimide (16): $^1$H-NMR (CDCl$_3$, 400 MHz): δ 1.29 (m, 4H), 1.68 (m, 6H), 1.80 (d, J=7.8 Hz, 3H), 1.84 (s, 3H), 3.24 (m, 1H), 6.53 (q, J=7.8 Hz, 1H), 8.37 (br s, 1H). $^{13}$C-NMR (CDCl$_3$, 100 MHz): δ 12.4, 14.6, 25.7, 26.0, 29.1, 44.5, 132.3, 134.8, 167.3, 179.4. HRMS calcd. for C$_{12}$H$_{19}$NO$_2$Na$^+$ is 232.1308 and observed=232.1300.

N-isobutyryl-2-methyl-2-butenimide (17): $^1$H-NMR (CDCl$_3$, 500 MHz): δ 1.10 (d, J=5.0 Hz, 6H), 1.74 (d, J=6.5 Hz, 3H), 1.80 (s, 3H), 3.46 (m, 1H), 6.53 (q, J=6.5 Hz, 1H), 8.85 (br s, 1H). $^{13}$C-NMR (CDCl$_3$, 125 MHz): δ 12.4, 14.6, 18.9, 34.8, 132.2, 135.0, 167.6, 180.9. HRMS calcd. for C$_9$H$_{15}$NO$_2$Na$^+$ is 192.0995 and observed=192.0992.

N-isobutyryl-2-ethyl-2-butenimide (20): $^1$H-NMR (CDCl$_3$, 400 MHz): δ 1.0 (t, J=7.5 Hz, 3H), 1.16 (d, J=7.0 Hz, 3H), 1.18 (d, J=6.0 Hz, 6H), 1.81 (q, J=7.5 Hz, 2H), 3.51 (m, 1H), 6.42 (q, J=7.0 Hz, 1H), 8.40 (br s, 1H). $^{13}$C-NMR (CDCl$_3$, 100 MHz): δ 13.4, 14.2, 18.9, 20.1, 34.8, 35.8, 133.6, 139.0, 167.2, 180.6. HRMS calcd. for C$_{10}$H$_{17}$NO$_2$Na$^+$ is 206.1151 and observed=206.1155.

N-isobutyryl-2-bromo-2-butenimide (21): $^1$H-NMR (CDCl$_3$, 500 MHz): δ 1.20 (d, J=6.0 Hz, 6H), 1.97 (d, J=7.0 Hz, 3H), 3.40 (m, 1H), 7.50 (q, J=7.0 Hz, 1H), 8.77 (br s, 1H). $^{13}$C-NMR (CDCl$_3$, 125 MHz): δ 18.3, 18.8, 35.2, 118.4, 141.7, 159.6, 178.9. HRMS calcd. for C$_8$H$_{12}$BrNO$_2$Na$^+$ is 255.9944 and observed=255.9956.

N-isobutyryl-2-phenyl-2-butenimide (22): $^1$H-NMR (CDCl$_3$, 500 MHz): δ 1.14 (d, J=6.5 Hz, 6H), 1.71 (d, J=7.0 Hz, 3H), 3.49 (m, 1H), 7.18 (m, 2H), 7.30 (m, 1H), 7.42 (m, 1H), 7.45 (m, 2H), 7.52 (br s, 1H). $^{13}$C-NMR (CDCl$_3$, 100 MHz): δ 15.8, 18.8, 35.1, 129.0, 129.6, 129.9, 134.1, 136.8, 140.9, 164.4, 179.5. HRMS calcd. for C$_{14}$H$_{17}$NO$_2$Na$^+$ is 254.1151 and observed=254.1151.

N-isobutyryl-2-methyl-2-pentenimide (23): $^1$H-NMR (CDCl$_3$, 400 MHz): δ 1.02 (t, J=7.6 Hz, 3H), 1.16 (d, J=6.4 Hz, 6H), 1.17 (m, 2H), 1.84 (s, 3H), 3.52 (m, 1H), 6.43 (t, J=6.8 Hz, 1H), 8.53 (br s, 1H). $^{13}$C-NMR (CDCl$_3$, 100 MHz): δ 12.6, 13.1, 18.9, 22.3, 33.9, 34.8, 130.8, 141.9, 167.6, 181.4. HRMS calcd. for C$_{10}$H$_{17}$NO$_2$Na$^+$ is 206.1151 and observed=206.1145.

N-isobutyryl-2-methyl-2-hexenimide (24): $^1$H-NMR (CDCl$_3$, 500 MHz): δ 0.95 (t, J=7.5 Hz, 3H), 1.18 (d, J=7 Hz, 6H), 1.48 (m, 2H), 1.87 (d, J=1 Hz, 3H), 2.17 (m, 2H), 3.54 (m, 1H), 6.44 (m, 1H), 8.22 (br s, 1H). $^{13}$C-NMR (CDCl$_3$, 125 MHz): δ 12.8, 14.1, 18.9, 22.0, 31.0, 34.9, 131.5, 140.1, 167.2, 180.4. HRMS calcd. for C$_{11}$H$_{19}$NO$_2$Na$^+$ is 220.1308 and observed=220.1311.

N-isobutyryl-2,4-dimethyl-2-pentenimide (25): $^1$H-NMR (CDCl$_3$, 500 MHz): δ 1.04 (d, J=6.5 Hz, 6H), 1.19 (d, J=7.0 Hz, 6H), 1.88 (d, J=1.5 Hz, 3H), 2.65 (m, 1H), 3.55 (m, 1H), 6.21 (m, 1H), 8.06 (br s, 1H). $^{13}$C-NMR (CDCl$_3$, 125 MHz):

δ 12.7, 18.9, 22.2, 28.4, 34.9, 129.3, 146.6, 167.5, 180.5. HRMS calcd. for $C_{11}H_{19}NO_2Na^+$ is 220.1308 and observed=220.1310.

N-isobutyryl-2,5-dimethyl-2-hexenimide (26): $^1$H-NMR (CDCl$_3$, 400 MHz): δ 0.92 (d, J=6.4 Hz, 6H), 1.18 (d, J=6.8 Hz, 6H), 1.73 (m, 1H), 1.85 (d, J=1.2 Hz, 3H), 2.07 (m, 2H), 3.53 (m, 1H), 6.44 (m, 1H), 8.02 (br s, 1H). $^{13}$C-NMR (CDCl$_3$, 100 MHz): δ 12.9, 18.9, 22.7, 28.5, 34.9, 38.1, 131.8, 139.2, 167.2, 180.4. HRMS calcd. for $C_{12}H_{21}NO_2Na^+$ is 234.1464 and observed=234.1468.

N-isobutyryl-2-methyl-2-decenimide (27): $^1$H-NMR (CDCl$_3$, 400 MHz): δ 0.88 (m, 3H), 1.15 (d, J=7.0 Hz, 6H), 1.28 (m, 10H), 1.44 (m, 2H), 1.86 (s, 3H), 3.54 (m, 1H), 6.44 (t, J=6.5 Hz, 1H), 8.17 (br s, 1H). $^{13}$C-NMR (CDCl$_3$, 100 MHz): δ 12.7, 14.3, 18.9, 22.8, 28.7, 29.0, 29.2, 29.5, 31.9, 33.9, 34.8, 131.2, 140.5, 167.3, 180.8. HRMS calcd. for $C_{15}H_{27}NO_2Na^+$ is 276.1934 and observed=276.1930.

N-isobutyryl-2-ethyl-2-pentenimide (28): $^1$H-NMR (CDCl$_3$, 400 MHz): δ 1.00 (t, J=7.6 Hz, 3H), 1.02 (t, J=7.2 Hz, 3H), 1.15 (d, J=6.8 Hz, 6H), 2.20 (m, 2H), 2.32 (q, J=7.6 Hz, 2H), 3.52 (m, 1H), 6.27 (t, J=7.6 Hz, 1H), 8.19 (br s, 1H). $^{13}$C-NMR (CDCl$_3$, 100 MHz): δ 13.6, 13.9, 18.9, 20.4, 21.9, 34.8, 137.8, 140.2, 167.2, 180.3. HRMS calcd. for $C_{11}H_{19}NO_2Na^+$ is 220.1307 and observed=220.1301.

N-isobutyryl-2-methyl-3-phenyl-2-propenimide (29): $^1$H-NMR (CDCl$_3$, 500 MHz): δ 1.23 (d, J=6.9 Hz, 6H), 2.15 (s, 3H), 3.58 (m, 1H), 7.35 (m, 6H), 8.15 (br s, 1H). $^{13}$C-NMR (CDCl$_3$, 125 MHz): δ 14.5, 19.0, 35.1, 128.8, 128.9, 129.8, 131.9, 135.4, 137.1, 167.9, 180.5. HRMS calcd. for $C_{14}H_{17}NO_2Na^+$ is 254.1151 and observed=254.1146.

N-isobutyryl-2,3-diphenyl-2-propenimide (30): $^1$H-NMR (CDCl$_3$, 400 MHz): δ 1.17 (d, J=6.5 Hz, 6H), 3.52 (m, 1H), 6.99 (s, 1H), 7.00 (m, 1H), 7.20 (m, 5H), 7.48 (m, 3H), 7.73 (br s, 1H), 7.93 (s, 1H). $^{13}$C-NMR (CDCl$_3$, 100 MHz): δ 18.9, 35.2, 128.6, 129.7, 130.0, 130.3, 130.9, 131.0, 133.8, 134.4, 134.9, 141.0, 164.9, 179.4. HRMS calcd. for $C_{19}H_{19}NO_2Na^+$ is 316.1308 and observed=316.1305.

General Procedure for the Conjugate Addition Reaction. Under nitrogen, a solution of 0.071 mmol of magnesium perchlorate or magnesium triflimide and 0.072 mmol of cyclopropyl bisoxazoline ligand in 2 mL dichloromethane was stirred for 30 minutes at room temperature. To this solution was added the imide substrate (0.236 mmol), and the reaction was stirred for an additional 30 minutes at room temperature. The reaction was cooled to −40° C. and stirred at that temperature for 30 minutes followed by the addition of N-benzyl hydroxyl amine (0.355 mmol in 1 mL of dichloromethane). After the reaction was judged complete (as determined by thin layer chromatography), it was quenched by the addition of trifluoroacetic acid (0.1 mL) at −40° C. The reaction was stirred for an additional 30 minutes and filtered through silica gel, and the solids were further washed with dichloromethane. Rotary evaporation of the organics gave a crude product, and the crude product was purified by flash chromatography using silica gel (15% ethyl acetate:hexane).

trans-2-Benzyl-3,4-dimethylisoxazolidin-5-one (19): $^1$H-NMR (CDCl$_3$, 400 MHz): δ 1.20 (d, J=7.2 Hz, 3H), 1.29 (d, J=6.0 Hz, 3H), 2.60 (dq, J=12.1 Hz, 7.0 Hz, 1H), 2.97 (m, 1H), 3.95 (d, J=14.2 Hz, 1H), 4.23 (d, J=14.2 Hz, 1H), 7.33 (m, 5H). Literature NMR for racemic 19 can be found in Niu et al., *J. Am. Chem. Soc.*, 121:2456ff (1999), which is hereby incorporated by reference. $^{13}$C-NMR (CDCl$_3$, 100 MHz): δ 11.6, 16.2, 44.2, 61.5, 69.2, 128.1, 128.7, 129.3, 135.7, 175.9. HRMS calcd. for $C_{12}H_{15}NO_2Na^+$ is 228.0995 and observed=228.0996. $[α]_D^{25}$=−120.5 (c 1.2, CHCl$_3$), ee 96%. (column chiralcel OD, solvent hexanes:isopropanol 95:5, flow rate 1 mL/min. R$^T$, minor enantiomer, 11.0 min; major enantiomer, 15.6 min).

trans-2-Benzyl-3-methyl,4-ethylisoxazolidin-5-one (31): $^1$H-NMR (CDCl$_3$, 400 MHz): δ 1.04 (t, J=7.5 Hz, 3H), 1.18 (m, 2H), 1.30 (d, J=6.5 Hz, 3H), 2.49 (dq, J=12.0 Hz, 7.1 Hz, 1H), 3.08 (m, 1H), 3.95 (d, J=14.0 Hz, 1H), 4.22 (d, J=14.0 Hz, 1H), 7.36 (m, 5H). $^{13}$C-NMR (CDCl$_3$, 100 MHz): δ 11.1 16.8, 20.2, 50.1, 61.5, 66.4, 128.0, 128.7, 129.2, 135.7, 173.0. HRMS calcd. for $C_{13}H_{17}NO_2Na^+$ is 242.1151 and observed=242.1153. $[α]_D^{25}$=−51.2 (c 0.74, CHCl$_3$) ee 86%. (column chiralcel OD, solvent hexanes:isopropanol 95:5, flow rate 1 mL/min. R$^T$, minor enantiomer, 10.3 min; major enantiomer, 15.8 min).

trans-2-Benzyl-3-methyl,4-bromo-isoxazolidin-5-one (32): $^1$H-NMR (CDCl$_3$, 500 MHz): δ 1.40 (d, J=7.0 Hz, 3H), 3.47 (m, 1H), 4.07 (d, J=14.5 Hz, 1H), 4.31 (d, J=14.5 Hz, 1H), 4.39 (d, J=10.5 Hz, 1H), 7.36 (m, 5H). $^{13}$C-NMR (CDCl$_3$, 125 MHz): δ 15.6, 45.6, 61.6, 70.1, 128.5, 128.8, 129.4, 134.6, 169.3. HRMS calcd. for $C_{11}H_{12}BrNO_2Na^+$ is 291.9944 and observed=291.9949. $[α]_D^{25}$=−133.3 (c 0.93, CHCl$_3$) ee 76%. (column chiralpack AD, solvent hexanes:isopropanol 98:2, flow rate 0.5 mL/min. R$^T$, minor enantiomer, 34.7 min; major enantiomer, 37.2 min).

trans-2-Benzyl-3-methyl-4-phenyl-isoxazolidin-5-one (33): $^1$H-NMR (CDCl$_3$, 400 MHz): δ 1.27 (d, J=6.4 Hz, 3H), 3.38 (m, 1H), 3.73 (d, J=12.4 Hz, 1H), 4.05 (d, J=14.4 Hz, 1H), 4.30 (d, J=14.4 Hz, 1H), 7.20 (m, 2H), 7.38 (m, 8H). $^{13}$C-NMR (CDCl$_3$, 100 MHz): δ 16.0, 56.4, 61.4, 70.1, 128.2, 128.5, 128.8, 129.2, 129.3, 129.4, 133.4, 135.5, 173.7. HRMS calcd. for $C_{17}H_{17}NO_2Na^+$ is 290.1151 and observed=290.1154. $[α]_D^{25}$=226.2 (c 0.99, CHCl$_3$) ee 90% (column chiralcel OD, solvent hexanes:isopropanol 95:5, flow rate 1 mL/min. R$^T$, minor enantiomer, 17.9 min; major enantiomer, 35.0 min).

trans-2-Benzyl-3-ethyl,4-methylisoxazolidin-5-one (34): $^1$H-NMR (CDCl$_3$, 400 MHz): δ 1.02 (t, J=7.2 Hz, 3H), 1.18 (m, 2H), 1.23 (d, J=6.0 Hz, 3H), 2.49 (m, 1H), 2.82 (dt, J=12.0 Hz, 7.0 Hz, 1H), 3.97 (d, J=14.0 Hz, 1H), 4.28 (d, J=14.0 Hz, 1H), 7.32 (m, 5H). $^{13}$C-NMR (CDCl$_3$, 100 MHz): δ 9.1, 12.8, 23.4, 41.2, 62.1, 73.8, 128.0, 128.7, 129.3, 135.9, 176.5. HRMS calcd. for $C_{13}H_{17}NO_2Na^+$ is 242.1151 and observed=242.1154. $[α]_D^{25}$=−125.8 (c 2.17, CHCl$_3$) ee 90%. (column chiralcel OD, solvent hexanes:isopropanol 94:6, flow rate 1 mL/min). R$^T$, minor enantiomer, 9.2 min; major enantiomer, 13.4 min).

trans-2-Benzyl-4-methyl-3-propyl-isoxazolidin-5-one (35): $^1$H-NMR (CDCl$_3$, 500 MHz): δ 0.97 (t, J=7.5 Hz, 3H), 1.26 (d, J=7.0 Hz, 3H), 1.50 (m, 2H), 1.67 (m, 2H), 2.74 (m, 1H), 2.97 (m, 1H), 3.93 (d, J=14.0 Hz, 1H), 4.25 (d, J=14.5 Hz, 1H), 7.36 (m, 5H). $^{13}$C-NMR (CDCl$_3$, 125 MHz): δ 12.9, 14.6, 18.4, 33.3, 42.1, 62.2, 72.9, 128.0, 128.7, 129.3, 135.9, 176.3. HRMS calcd. for $C_{14}H_{19}NO_2Na^+$ is 256.1308 and observed=256.1304. $[α]_D^{25}$=191.3 (c 1.03, CHCl$_3$) ee 89% (column chiralcel OD, solvent hexanes:isopropanol 95:5, flow rate 1 mL/min. R$^T$, minor enantiomer, 12.5 min; major enantiomer, 17.8 min).

trans-2-Benzyl-3-isopropyl-4-methyl-isoxazolidin-5-one (36): $^1$H-NMR (CDCl$_3$, 500 MHz): δ 1.04 (d, J=7.0 Hz, 3H), 1.06 (d, J=6.5 Hz, 3H), 1.29 (d, J=7.0 Hz, 3H), 1.98 (m, 1H), 2.81 (m, 1H), 2.91 (dd, J=10.5 Hz, 3.5 Hz, 1H), 3.94 (d, J=14.0 Hz, 1H), 4.25 (d, J=14.5 Hz, 1H), 7.34 (m, 5H). $^{13}$C-NMR (CDCl$_3$, 125 MHz): δ 15.2, 17.7, 19.6, 29.3, 38.6, 63.1, 77.4, 128.0, 128.7, 129.3, 135.9, 177.0. HRMS calcd. for $C_{14}H_{19}NO_2Na^+$ is 256.1308 and observed=256.1325. $[α]_D^{25}$=−176.6 (c 0.99, CHCl$_3$) ee 81% (column chiralcel OD, solvent hexanes:isopropanol 95:5, flow rate 1 mL/min. $R^T$, minor enantiomer, 9.6 min; major enantiomer, 12.3 min).

trans-2-Benzyl-3-isobutyl-4-methyl-isoxazolidin-5-one (37): $^1$H-NMR (CDCl$_3$, 400 MHz): δ 0.96 (t, J=6.4 Hz, 6H), 1.28 (d, J=7.2 Hz, 3H), 1.59 (t, J=6.0 Hz, 2H), 1.82 (m, 1H), 2.67 (m, 1H), 3.00 (m, 1H), 3.90 (d, J=14.4 Hz, 1H), 4.24 (d, J=14.4 Hz, 1H), 7.30 (m, 5H). $^{13}$C-NMR (CDCl$_3$, 100 MHz): δ 13.3, 23.1, 23.7, 25.3, 41.5, 43.4, 62.3, 71.4, 128.0, 128.7, 129.2, 135.9, 176.3. HRMS calcd. for $C_{15}H_{21}NO_2Na^+$ is 270.1464 and observed=270.1464. $[\alpha]_D^{25}$=−114.2 (c 1.0, CHCl$_3$) ee 77% (column chiralcel OD, solvent hexanes:isopropanol 95:5, flow rate 1 mL/min. $R^T$, minor enantiomer, 7.5 min; major enantiomer, 10.7 min).

trans-2-benzyl-3-heptyl-4-methylisoxazolidin-5-one (38): $^1$H-NMR (CDCl$_3$, 400 MHz): δ 0.85 (t, J=4.0 Hz, 3H), 0.89 (d, J=5.0 Hz, 3H), 1.27 (m, 10H), 1.83 (m, 2H), 2.78 (m, 1H), 2.98 (m, 1H), 3.95 (d, J=14.0 Hz, 1H), 4.26 (d, J=14.0 Hz, 1H), 7.36 (m, 5H). $^{13}$C-NMR (CDCl$_3$, 100 MHz): δ 12.9, 14.3, 22.8, 24.9, 29.3, 30.0, 31.0, 31.9, 42.0, 62.2, 73.1, 128.0, 128.7, 129.3, 135.9, 176.4. HRMS calcd. for $C_{18}H_{27}NO_2Na^+$ is 312.1934 and observed=312.1930. $[\alpha]_D^{25}$=−18.9 (c 2.96, CHCl$_3$) ee 87% (column chiralcel OD, solvent hexanes:isopropanol 94:6, flow rate 1 mL/min. $R^T$, minor enantiomer, 7.1 min; major enantiomer, 9.5 min).

trans-2-benzyl-3,4-diethylisoxazolidin-5-one (39): $^1$H-NMR (CDCl$_3$, 400 MHz): δ 1.03 (t, J=9.6 Hz, 3H), 1.06 (t, J=9.6 Hz, 3H), 1.71 (m, 2H), 1.73 (m, 2H), 2.71 (m, 1H), 3.09 (m, 1H), 3.94 (d, J=14.0 Hz, 1H), 4.22 (d, J=14.0 Hz, 1H), 7.31 (m, 5H). $^{13}$C-NMR (CDCl$_3$, 100 MHz): δ 9.1, 10.9, 21.0, 23.9, 46.8, 62.3, 70.2, 128.0, 128.7, 129.3, 135.9, 175.9. HRMS calcd. for $C_{14}H_{19}NO_2Na^+$ is 256.1307 and observed=256.1296. $[\alpha]_D^{25}$=−73.5 (c 1.16, CHCl$_3$) ee 60% (column chiralcel OD, solvent hexanes:isopropanol 95:5, flow rate 1 mL/min. $R^T$, minor enantiomer, 8.7 min; major enantiomer, 13.7 min).

trans-2-Benzyl-4-methyl-3-phenyl-isoxazolidin-5-one (40): $^1$H-NMR (CDCl$_3$, 500 MHz): δ 1.20 (d, J=6.5 Hz, 3H), 2.99 (m, 1H), 3.84 (d, J=12.0 Hz, 1H), 3.88 (d, J=14.5 Hz, 1H), 4.16 (d, J=14.5 Hz, 1H), 7.29 (m, 5H), 7.41 (m, 3H), 7.49 (m, 2H). Literature NMR for racemic 40 can be found in Moglioni et al., *J. Org. Chem.*, 67:2402ff (2002), which is hereby incorporated by reference. $^{13}$C-NMR (CDCl$_3$, 125 MHz): δ 11.3, 46.2, 61.1, 78.1, 127.9, 128.0, 128.6, 129.3, 129.4, 129.4, 135.7, 135.9, 175.3. HRMS calcd. for $C_{17}H_{17}NO_2Na^+$ is 290.1151 and observed=290.1156. $[\alpha]_D^{25}$=−13.93 (c 0.92, CHCl$_3$) ee 76% (column chiralcel OD, solvent hexanes:isopropanol 95:5, flow rate 1 mL/min. $R^T$, minor enantiomer, 9.5 min; major enantiomer, 12.1 min).

trans-2-Benzyl-3,4-diphenylisoxazolidin-5-one (41): $^1$H-NMR (CDCl$_3$, 400 MHz): δ 3.95 (d, J=14.0 Hz, 1H), 4.14 (d, J=9.0 Hz, 1H), 4.22 (d, J=14.0 Hz, 1H), 4.27 (d, J=9.0 Hz, 1H), 7.33 (m, 15H). $^{13}$C-NMR (CDCl$_3$, 100 MHz): δ 57.9, 61.0, 78.7, 127.9, 128.1, 128.5, 128.7, 129.0, 129.1, 129.2, 129.4, 129.9, 132.8, 135.2, 135.5, 173.0. HRMS calcd. for $C_{22}H_{19}NO_2Na^+$ is 352.1307 and observed=352.1300. $[\alpha]_D^{25}$=35.3 (c 1.18, CHCl$_3$) ee 84% (column chiralcel OD, solvent hexanes:isopropanol 94:6, flow rate 1 mL/min. $R^T$, minor enantiomer, 14.9 min; major enantiomer, 19.3 min).

General Procedure for the Synthesis of Amino Acid. 0.5 mmol of isoxazolidin-5-one was dissolved in 3 mL of 90% aq. dioxane and added to a suspension of 20 mg. of 10% Pd/C in 3 mL of 90% aq. dioxane. The sample was heated at 60° C. for 16 hours under an ambient pressure of hydrogen. After the reaction was complete, it was filtered through celite, and the solvents were removed under vacuum to give the amino acid (90% yield). The product amino acids undergo enantioenrichment during recrystallization.

(R,R)-3-Amino-2-methyl butanoic acid (42): $^1$H-NMR (D$_2$O, 400 MHz): δ 1.07 (d, J=7.2 Hz, 3H), 1.17 (d, J=7.0 Hz, 3H), 2.32 (m, 1H), 3.29 (m, 1H). $^{13}$C-NMR (D$_2$O, 100 MHz): δ 16.8, 18.9, 47.6, 52.7, 184.3. HRMS calcd. for $C_5H_{11}NO_2Na^+$ is 140.0682 and observed=140.0687. $[\alpha]_D^{25}$=−8.0 (c 1, H$_2$O) (19 was 96% ee). Literature (Cardillo et al., *J. Org. Chem.*, 61:8651ff (1996), which is hereby incorporated by reference): $[\alpha]_D^{25}$=−8.7 (c 1.2, H$_2$O); ee 100%.

The absolute configuration of some of the isoxazolidinones was determined by conversion to known compounds.

General Procedure for Acetylation of Amino Acid. 1 mmol of 3-amino-2-ethyl butanoic acid (ee 86%) was added in one portion to a stirred solution of pyridine (2 mL), acetic anhydride (2 mL), and dimethylamino pyridine (5 mg) at room temperature. After 2 hours, the reaction mixture was quenched with water and extracted with ethyl acetate. The product was purified by flash chromatography on silica gel.

General Procedure for Esterification of the Amino Acid. A solution of SOCl$_2$ (2 mmol) in methanol (5 mL) was stirred for 2 h at −15° C. Then, the N-acetylamino acid was added in one portion and allowed to react overnight while slowly being warmed. The solvent was evaporated, and the residue was purified by flash chromatography using silica gel (30% ethyl acetate:hexane) to yield 80% of the product. The final product was recrystallized and underwent enantioenrichment.

(R,R)-Methyl-N-acetyl-2-ethyl-3-amino-butanoate (43):

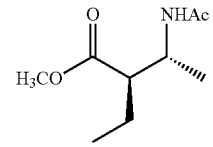

43

$^1$H-NMR (CDCl$_3$, 400 MHz): δ 0.92 (t, J=7.4 Hz, 3H), 1.11 (d, J=6.8 Hz, 3H), 1.57 (m, 2H), 1.96 (s, 3H), 2.38 (m, 1H), 3.69 (s, 3H), 4.23 (m, 1H), 6.4 (br s, 1H). $^{13}$C-NMR (CDCl$_3$, 100 MHz): δ 12.2, 23.6, 25.8, 29.9, 45.3, 50.8, 51.6, 169.6, 176.4. HRMS calcd. for $C_9H_{17}NO_3Na^+$ is 210.1100 and observed=210.1097. $[\alpha]_D^{25}$=15.0 (c 0.2, CHCl$_3$). Literature (Cardillo et al., *J. Org. Chem.*, 61:8651ff (1996), which is hereby incorporated by reference): $[\alpha]_D^{25}$=14.3 (c 0.3, CHCl$_3$); ee 94%.

(2S,3S) 3-tert-Butoxycarbonylamino-2,4-dimethyl-pentanoic acid methyl ester (44) was prepared using the procedure outlined in Scheme IV.

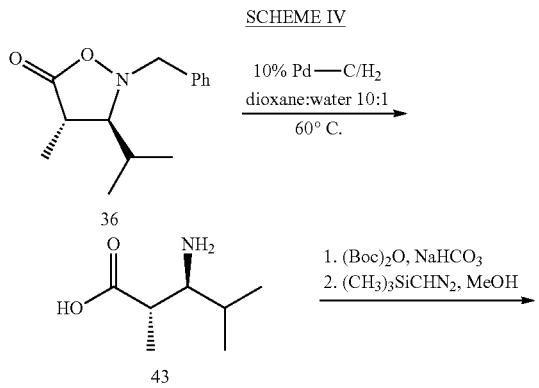

31

-continued

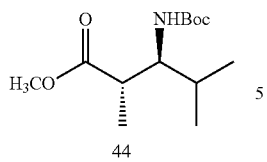

44

Briefly, isoxazolidinone 36 (70% ee) was converted to β-amino acid 43 using the procedure described above. Amino acid 43 (0.075 g, 0.517 mmol) was dissolved in a solution of NaHCO$_3$ (0.11 g, 1.29 mmol) in water (5 mL). To the solution, (Boc)$_2$O (0.17 g, 0.77 mmol) was added as solution in THF (2 mL). The reaction mixture was stirred at room temperature for 12 hours and then extracted with CH$_2$Cl$_2$ (2×5 mL). The aqueous layer was then acidified with 10% KHSO$_4$ solution. The precipitated N-Boc protected amino acid was extracted with CH$_2$Cl$_2$ (4×5 mL). The organic extracts were combined, dried on anhydrous Na$_2$SO$_4$, and concentrated under vacuum to afford almost pure N-Boc amino acid that was used without purification. N-Boc amino acid was dissolved in dry methanol (5 mL) under N$_2$. The solution was cooled to 0° C. To the cold solution, a 2M solution of (CH$_3$)$_3$SiCHN$_2$ in ether was added drop-wise until a yellow color persisted. The reaction mixture was stirred at 0° C. for 30 minutes; the solvent was removed under vacuum; and the residue was chromatographed on silica gel column (2% ethyl acetate in hexanes) to afford pure methyl ester as an oily liquid. Yield 80%. $[\alpha]_D^{20}$=−23.6 (c 1.0, chloroform). Literature (Seebach et al., *Helv. Chim. Acta*, 81:932ff (1998), which is hereby incorporated by reference): $[\alpha]_D^{20}$=−34.9 (c 1, chloroform) for absolute configuration (2S,3S). Therefore, absolute configuration of methyl ester and hence of isoxazolidinone was deemed to be (2S,3S). 43: $^1$H-NMR (CDCl$_3$, 400 MHz): δ 0.89 (t, J=6.4 Hz, 6H), 1.18 (d, J=6.8 Hz, 3H), 1.41 (s, 8H) & 1.43 (s, 1H) rotational isomers, 1.63 (m, 1H), 2.76 (m, 1H), 3.37 (m, 1H), 3.64 (s, 3H), 5.20 (d, J=10 Hz, 1H); $^{13}$C-NMR (CDCl$_3$, 100 MHz): δ 15.8, 19.3, 20.1, 28.6, 31.9, 40.7, 51.8, 58.8, 79.0, 156.6, 176.4. HRMS calcd. for C$_{13}$H$_{25}$NO$_4$Na$^+$ is 282.1676 and observed=282.1673.

(2R,3R) 3-tert-Butoxycarbonylamino-2,5-dimethyl-hexanoic acid methyl ester (46) was prepared using the procedure outlined in Scheme V.

SCHEME V

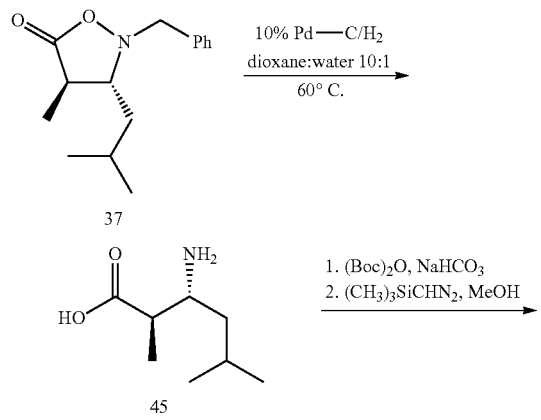

32

-continued

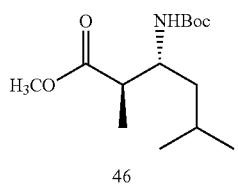

46

Briefly, isoxazolidinone 37 (52% ee) was converted to the amino acid 45 and then to the ester 46 following the same procedure as set forth above. $[\alpha]_D^{20}$=13.8 (c 1, chloroform). Literature (Seebach et al., *Helv. Chim. Acta*, 81:932ff (1998), which is hereby incorporated by reference): $[\alpha]_D^{20}$=−43.0 (c 1, chloroform) for absolute configuration (2S,3S). Therefore, absolute configuration of methyl ester and hence of isoxazolidinone was deemed to be (2R,3R). 46: $^1$H-NMR (CDCl$_3$, 300 MHz): δ 0.89 (d, J=4.8 Hz, 3H), 0.91 (d, J=4.5 Hz, 3H), 1.19 (d+m, J=7.2 Hz for d, 3H+1H), 1.32 (m, 1H), 1.43 (s, 8H) & 1.46 (s, 1H) rotational isomers, 1.62 (m, 1H), 2.63 (m, 1H), 3.68 (s, 3H), 3.83 (m, 1H), 5.02 (d, J=10.0 Hz, 1H). $^{13}$C-NMR (CDCl$_3$, 100 MHz): δ 14.6, 22.3, 23.3, 25.1, 28.6, 43.3, 43.5, 50.9, 51.7, 79.1, 156.1, 176.0. HRMS calcd. for C$_{14}$H$_{27}$NO$_4$Na$^+$ is 296.1832 and observed=296.1830.

3-Amino-2-methyl-3-phenyl-propionic acid methyl ester (48) was prepared using the procedure outlined in Scheme VI.

SCHEME VI

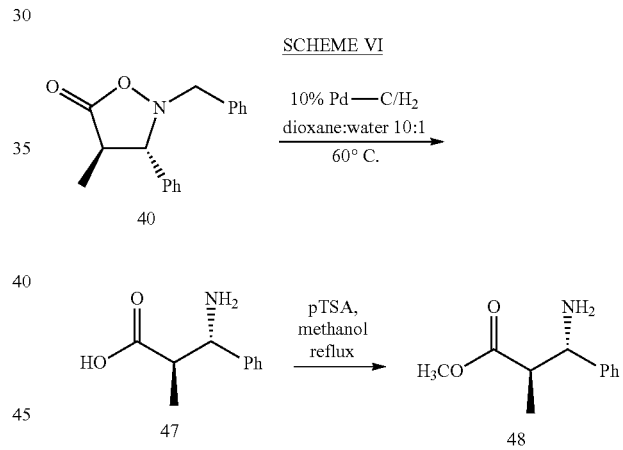

Briefly, isoxazolidinone 40 (>99% ee) was converted to the amino acid 47 following the same procedure as set forth above. The mixture of amino acid 47 (0.07 g, 0.36 mmol) and pTSA (0.15 g, 0.79 mmol) was dissolved in dry methanol (5 mL) and refluxed for 12 hours. Methanol was removed under vacuum, and the residue was basified with 10% aqueous NaHCO$_3$ solution. The precipitated aminoester was extracted with CH$_2$Cl$_2$ (3×5 mL). Organic extracts were combined and dried on anhydrous Na$_2$SO$_4$. Solvent was removed under vacuum to afford pure methyl ester 48 as an oily liquid. $[\alpha]_D^{20}$=−31.7 (c 1.04, chloroform). Literature (Davies et al., *J. Chem. Soc. Chem. Commun.*, 1153ff (1993), which is hereby incorporated by reference): $[\alpha]_D^{20}$=−29.2 (c 1.00, chloroform) for absolute configuration (2R,3S). Therefore, absolute configuration of methyl ester and hence of isoxazolidinone was deemed to be (2R,3S).

Example 3

Conjugate Addition on Cycloalkylene Carboxylates

Following the methods described in Examples 1 and 2 hereinabove, α,β-unsaturated imides that are substituted in the α and β positions with groups which, together with the carbon atoms at the α and β positions, form a ring are used to prepare β-amino acids that are substituted in the α and β positions with groups which, together with the carbon atoms at the α and β positions, form a ring.

More particularly, conjugate addition on cyclohexene carboxylates was carried out to produce 50 from imide 49 as described in Table 3.

TABLE 3

| Entry | R | Lewis Acid | time (h) | T °C. | Yield | de | ee |
|---|---|---|---|---|---|---|---|
| 1 | isopropyl | $Mg(ClO_4)_2$ | 18 | 0 | 30 | >95 | 57 |
| 2 | cyclohexyl | $Mg(ClO_4)_2$ | 18 | 0 | 37 | >95 | 43 |
| 3 | isopropyl | $Mg(NTf_2)_2$ | 18 | 0 | 39 | >95 | 59 |
| 4 | cyclohexyl | $Mg(NTf_2)_2$ | 18 | 0 | 40 | >95 | 60 |

The reaction rates were found to be slow compared to α,β-unsaturated imides derived from tiglates, and large amount of the 1,2-adduct were observed. It was found that reaction at 0° C. resulted in about 30-40% yield with about 40-60% ee and that the use of $Mg(NTf_2)_2$ produced better enantioselectivities than $Mg(ClO_4)_2$. Catalytic hydrogenation of 50 produces β-amino acid 51.

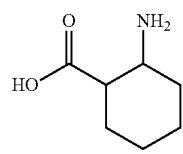

51

Conjugate addition on cyclopentene carboxylates was carried out to produce 53 from imide 52 as described in Table 4.

TABLE 4

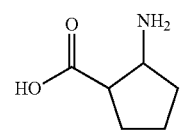

52

53

| Entry | R | Lewis Acid | time (h) | T °C. | Yield | de | ee |
|---|---|---|---|---|---|---|---|
| 1 | isopropyl | $Mg(ClO_4)_2$ | 24 | −40 | 90 | >95 | 84 |
| 2 | cyclohexyl | $Mg(ClO_4)_2$ | 24 | −40 | 75 | >95 | 79 |
| 3 | isopropyl | $Mg(NTf_2)_2$ | 24 | −40 | 90 | >95 | 94 |
| 4 | cyclohexyl | $Mg(NTf_2)_2$ | 24 | −40 | 78 | >95 | 90 |

Good reaction rates and excellent selectivities were observed. The isopropyl template was found to be better than the cyclohexyl template, and the use of $Mg(NTf_2)_2$ produced better enantioselectivities than $Mg(ClO_4)_2$. Catalytic hydrogenation of 53 produces β-amino acid 54.

54

Example 4

Preparation of α-Alkoxy-β-substituted-β-amino Acids

Following the methods described in Examples 1 and 2 hereinabove, α-alkoxy-β-substituted-α,β-unsaturated imides are used to prepare α-alkoxy-β-substituted-β-amino acids.

More particularly, imide 55 was cyclized to produce 2-benzyl-3-substituted-4-alkoxy-isoxazolidin-5-one 56 as described in Table 5.

TABLE 5

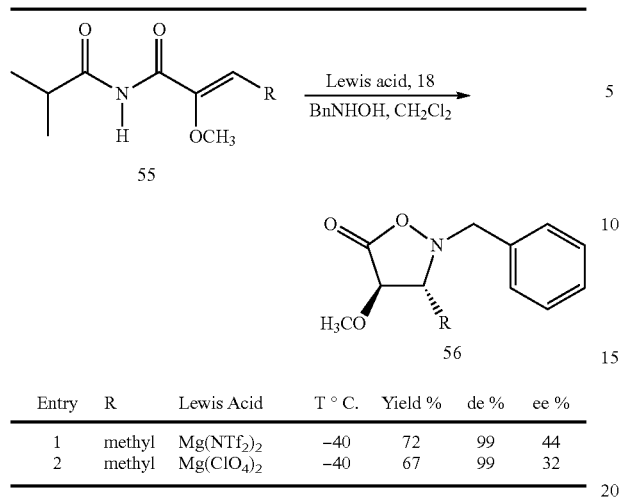

| Entry | R | Lewis Acid | T ° C. | Yield % | de % | ee % |
|---|---|---|---|---|---|---|
| 1 | methyl | Mg(NTf$_2$)$_2$ | −40 | 72 | 99 | 44 |
| 2 | methyl | Mg(ClO$_4$)$_2$ | −40 | 67 | 99 | 32 |

Catalytic hydrogenation of 56 produces β-amino acid 57.

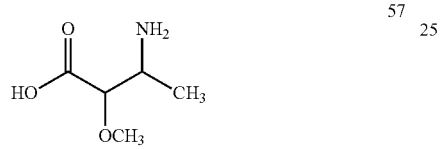

Example 5

Preparation of α-Halo-β-substituted-β-amino Acids

Following the methods described in Examples 1 and 2 hereinabove, α-halo-β-substituted-α,β-unsaturated imides are used to prepare α-halo-β-substituted-β-amino acids.

More particularly, imide 58 was cyclized to produce 2-benzyl-3-substituted-4-halo-isoxazolidin-5-one 59 as described in Table 6.

TABLE 6

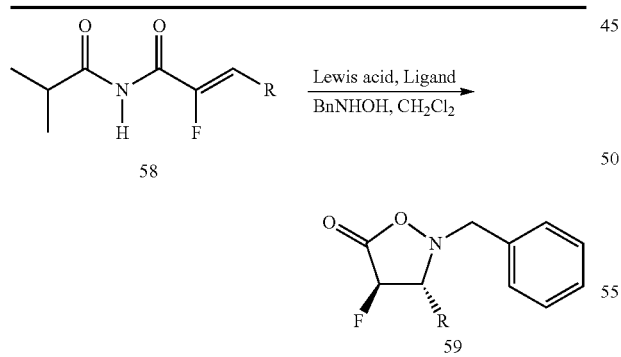

| Entry | Ligand | R | Lewis Acid | Yield % | de % | ee % |
|---|---|---|---|---|---|---|
| 1 | 18 | phenyl | Mg(ClO$_4$)$_2$ | 65 | 99 | 6 |
| 2 | 18 | phenyl | Mg(NTf$_2$)$_2$ | 69 | 99 | 9 |
| 3 | 18 | phenyl | Zn(OTf$_2$)$_2$ | — | — | — |
| 4 | 60 | phenyl | Mg(ClO$_4$)$_2$ | 56 | 99 | 7 |
| 5 | 61 | phenyl | Mg(ClO$_4$)$_2$ | 33 | 99 | 13 |
| 6 | 18 | ethyl | Mg(ClO$_4$)$_2$ | 80 | 34 | 8 |
| 7 | 18 | ethyl | Mg(NTf$_2$)$_2$ | 80 | 42 | 18 |

Ligands 60 and 61 have the following formulae:

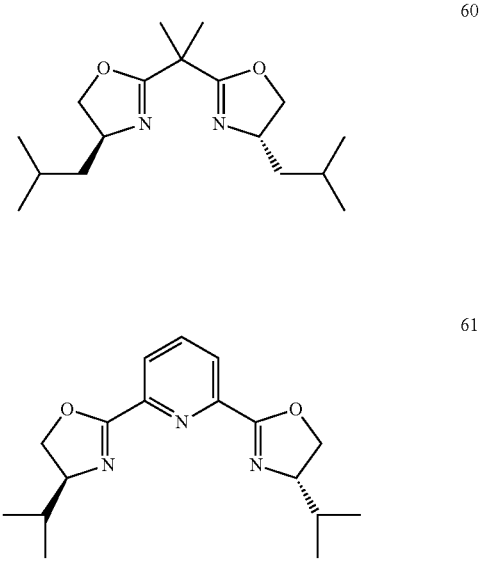

As Table 6 shows, although α-halo-β-substituted-α,β-unsaturated imides can be converted to the corresponding 2-benzyl-3-substituted-4-halo-isoxazolidin-5-one using the methods of the present invention, enantioselectivity for these reactions appears to be poor. Catalytic hydrogenation of 59 produces β-amino acid 62.

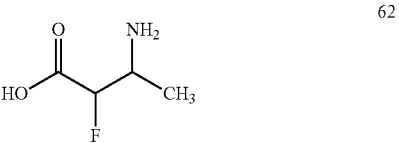

Example 6

Preparation of α-Unsubstituted-β-substituted-β-amino Acids

Following the methods described in Examples 1 and 2 hereinabove, α-unsubstituted-β-substituted-α,β-unsaturated imides are used to prepare α-unsubstituted-β-substituted-β-amino acids.

More particularly, imide 63 was cyclized to produce 2-benzyl-3-substituted-4-unsubstituted-isoxazolidin-5-one 64 using Mg(NTf$_2$)$_2$ and Mg(ClO$_4$)$_2$ Lewis acids as described in Tables 7 and 8, respectively.

TABLE 7

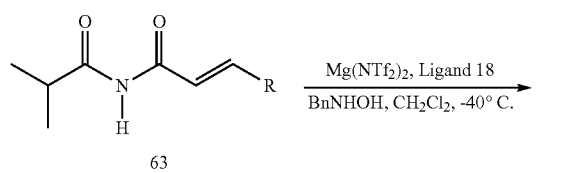

| Entry | R | Time (hours) | Yield % | ee % |
|---|---|---|---|---|
| 1 | methyl | 8 | 79 | 94 |
| 2 | ethyl | 8 | 68 | 96 |
| 3 | n-propyl | 8 | 78 | 97 |
| 4 | phenyl | 8 | 80 | 90 |
| 5 | 3-(3,4-methylenedioxy-phenyl) | 16 | 72 | 94 |
| 6 | 3-furan | 20 | 74 | 78 |
| 7 | 3-furan | 40 (at −60° C.) | 69 | 84 |

TABLE 8

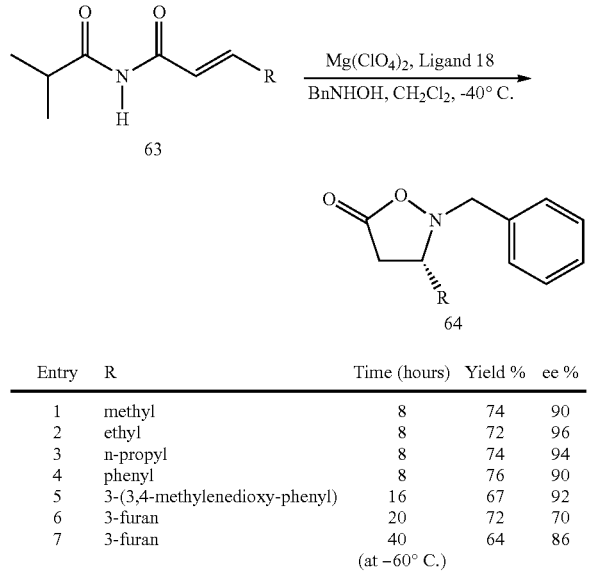

| Entry | R | Time (hours) | Yield % | ee % |
|---|---|---|---|---|
| 1 | methyl | 8 | 74 | 90 |
| 2 | ethyl | 8 | 72 | 96 |
| 3 | n-propyl | 8 | 74 | 94 |
| 4 | phenyl | 8 | 76 | 90 |
| 5 | 3-(3,4-methylenedioxy-phenyl) | 16 | 67 | 92 |
| 6 | 3-furan | 20 | 72 | 70 |
| 7 | 3-furan | 40 (at −60° C.) | 64 | 86 |

As Tables 7 and 8 show, using the methods of the present invention, 2-benzyl-3-substituted-4-unsubstituted-isoxazolidin-5-ones are produced in good yield and with high enantioselectivity. Catalytic hydrogenation of 64 produces β-amino acid 65.

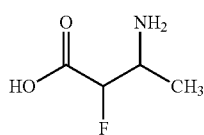

Example 7

Preparation of α-Substituted-β-unsubstituted-β-amino Acids

Following the methods described in Examples 1 and 2 hereinabove, α-substituted-β-unsubstituted-α,β-unsaturated imides are used to prepare α-substituted-β-unsubstituted-β-amino acids.

More particularly, imide 66 was cyclized to produce 2-benzyl-3-unsubstituted-4-substituted-isoxazolidin-5-one 67 using Mg(NTf$_2$)$_2$ and Mg(ClO$_4$)$_2$ Lewis acids as described in Tables 9 and 10, respectively.

TABLE 9

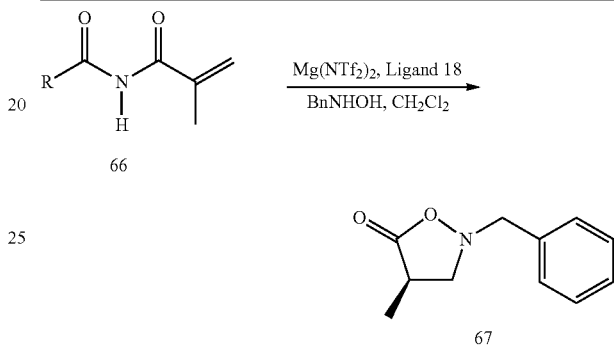

| Entry | R | T (° C.) | time (hours) | Yield % | ee % |
|---|---|---|---|---|---|
| 1 | i-propyl | −40 | 6 | 76 | 50 |
| 2 | i-propyl | −60 | 12 | 57 | 58 |
| 3 | phenyl | −40 | 8 | 67 | 28 |
| 4 | t-butyl | −40 | 16 | 72 | 56 |
| 5 | t-butyl | −60 | 20 | 42 | 32 |
| 6 | Bn—O— | 0 | 20 | 36 | 38 |
| 7 | PPh$_2$ | −40 | 72 | 5 | — |
| 8 | methyl | −40 | 6 | 46 | 50 |

TABLE 10

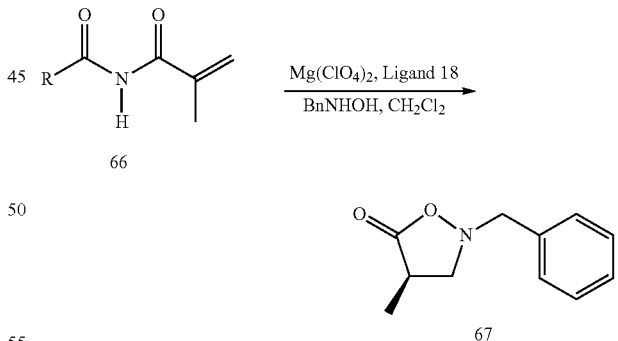

| Entry | R | T (° C.) | time (hours) | Yield % | ee % |
|---|---|---|---|---|---|
| 1 | i-propyl | −40 | 6 | 72 | 40 |
| 2 | i-propyl | −60 | 12 | 54 | 60 |
| 3 | phenyl | −40 | 8 | 63 | 26 |
| 4 | t-butyl | −40 | 16 | 74 | 60 |
| 5 | t-butyl | −60 | 20 | 48 | 42 |
| 6 | Bn—O— | 0 | 20 | 40 | 22 |
| 7 | PPh$_2$ | −40 | 72 | 5 | — |
| 8 | methyl | −40 | 6 | 38 | 24 |

Tables 9 and 10 show that α-substituted-β-unsubstituted-α,β-unsaturated imides can be readily converted to 2-benzyl-3- unsubstituted-4-substituted-isoxazolidin-5-ones. Catalytic hydrogenation of 2-benzyl-3-unsubstituted-4-substituted-isoxazolidin-5-ones 67 produces β-amino acid 68.

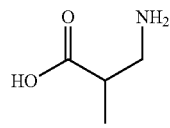

68

Example 8

Preparation of α,α-Disubstituted-β-substituted-β-amino Acids

2-Benzyl-3-substituted-4,4-disubstituted-isoxazolidin-5-ones 70-72 were prepared from 2-benzyl-3-substituted-4-monosubstituted-isoxazolidin-5-one 69 by LiHMDS-mediated alkylation, as described in the following Scheme VII.

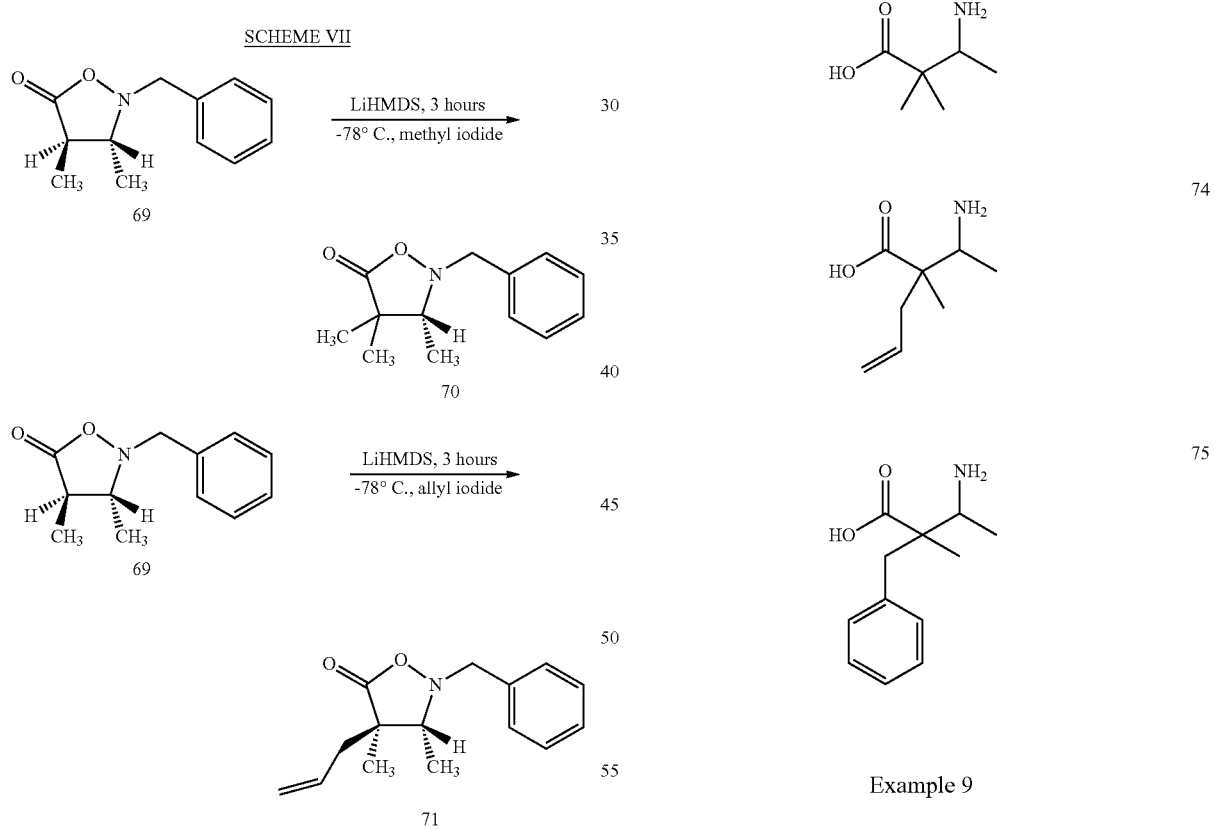

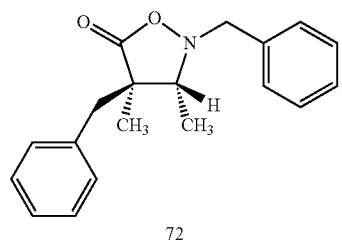

72

2-Benzyl-3-methyl-4,4-dimethyl-isoxazolidin-5-one 70 was produced in 38% yield. 2-Benzyl-3-methyl-4-methyl-4-allyl-isoxazolidin-5-one 71 was produced in 35% yield. 2-Benzyl-3-methyl-4-methyl-4-benzyl-isoxazolidin-5-one 72 was produced in 20% yield.

Catalytic hydrogenation of 2-benzyl-3-substituted-4,4-disubstituted-isoxazolidin-5-ones 70-72 produces α,α-disubstituted-β-substituted-β-amino acids 73-75, respectively.

Example 9

Preparation of the cis-Diastereomer of β-Amino Acids

A variety of trans-2-substituted-3-monosubstituted-4-monosubstituted-isoxazolidin-5-ones 76 were converted to their respective cis-diastereomers 77 by treatment with LiHMDS followed by quenching with acid. The preparative protocol is set forth in Table 11, along with the results of these experiments.

TABLE 11

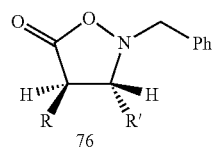

| Entry | R | R' | Quenching acid | Yield % 77 | Yield % aza 78 |
|---|---|---|---|---|---|
| 1 | Ph | Me | acetic acid | 50 | 10 |
| 2 | Ph | Me | trifluoroacetic acid | 20 | n.d. |
| 3 | Ph | Me | tris-t-butyl phenol | 20 | n.d. |
| 4 | Ph | Me | triphenylacetic acid | 20 | n.d. |
| 5 | Me | Me | acetic acid | 30 | 15 |
| 6 | Me | Me | trifluoroacetic acid | 10 | n.d. |
| 7 | Me | Me | tris-t-butyl phenol | 20 | n.d. |
| 8 | Me | Me | triphenylacetic acid | 20 | n.d. |
| 9 | Me | Ph | acetic acid | 25 | 25 |
| 10 | Me | Et | acetic acid | 58 | 10 |

The experiment set forth in entry 5 of Table 11 was repeated using various other quenching temperatures to determine the effect of quenching temperature on yield of aza 78. Aza 78 yield at −78° C., −40° C., and 0° C. was found to be <10%, <10%, and 35%, respectively.

Catalytic hydrogenation of trans-2-substituted-3-mono-substituted-4-monosubstituted-isoxazolidin-5-ones 77 produces the cis-diastereomers of β-amino acids 79.

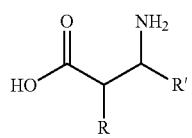

79

Example 10

Preparation of Other β-Amino Acids

Following the methods described in examples 1 and 2 hereinabove, β-amino acids 80-91, as shown in Scheme VIII, have been or can be prepared.

Scheme VIII

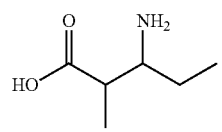

80

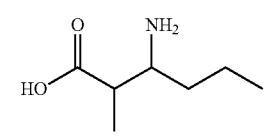

81

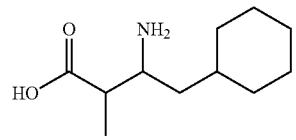

82

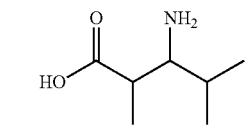

83

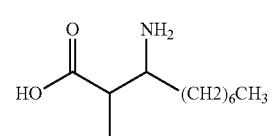

84

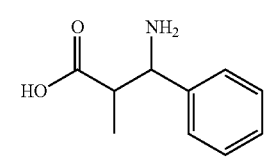

85

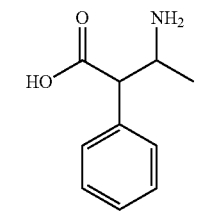

86

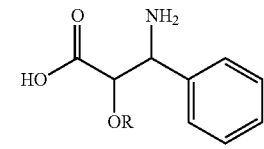

87

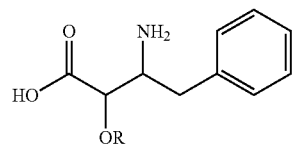

88

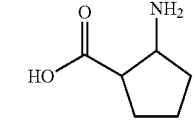

89

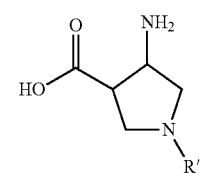

90

-continued

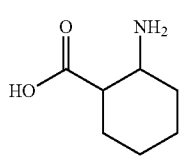

91

In Scheme VIII, R is H, an alkyl group, an aryl group, or another hydroxy protecting group, and R' is H, an alkyl group, an aryl group, or another amine protecting group.

Example 11

Tentative Model for Observed Stereochemistry

While not intending to be limited by any particular model or any particular mechanism, we have developed a tentative cis octahedral model 92 for the observed stereochemistry based on the identity of 42 (in Scheme III of Example 1).

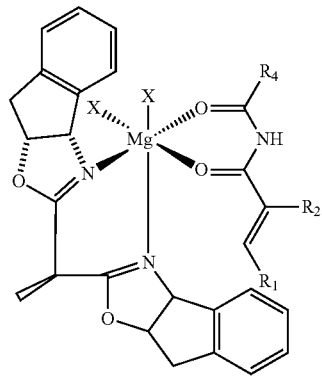

92

Interestingly, the addition of nitrogen occurs on the re face of the β-carbon, as is also the case for additions of both amines (Sibi et al., *Org. Lett.*, 2:3393ff (2000), which is hereby incorporated by reference), and radicals (Sibi et al., *J. Am. Chem. Soc.*, 123:9472ff (2001), which is hereby incorporated by reference) to oxazolidinone crotonates and cinnamates when activated by $MgX_2/18$. This suggests by analogy that, even in the case of tiglates, reaction still occurs from s-cis rotamers 6 rather than from s-trans rotamers 7 shown in Scheme II. The high diastereoselectivity may result from the fact that protonation of the α-carbon is concerted with addition of nitrogen to the βcarbon.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A method for preparing a β-amino acid, said method comprising:
   reacting an α,β-unsaturated imide with a substituted hydroxyl amine in the presence of a chiral Lewis acid to yield a chiral 2-substituted-isoxazolidin-5-one; and
   converting the chiral 2-substituted-isoxazolidin-5-one to a β-amino acid; provided that at least one of the following three conditions is met: (i) a hydrogen atom is bonded to the α,β-unsaturated imide's imide nitrogen; (ii) the β-amino acid is an α-substituted-β-amino acid; or (iii) the β-amino acid is an β-unsubstituted-β-amino acid.

2. A method according to claim 1, wherein a hydrogen atom is bonded to the α,β-unsaturated imide's imide nitrogen.

3. A method according to claim 1, wherein the chiral Lewis acid is a chiral Lewis acid complex.

4. A method according to claim 1, wherein said converting the 2-substituted-isoxazolidin-5-one to the β-amino acid is carried out by hydrogenation.

5. A method according to claim 4, wherein said converting chiral Lewis acid comprises a chiral Lewis acid complex.

6. A method according to claim 1, wherein the β-amino acid is an α-substituted-β-amino acid.

7. A method according to claim 1, wherein the β-amino acid is an α-substituted-β-amino acid bearing an alkyl substituent in the α position.

8. A method according to claim 1, wherein the β-amino acid is an α-substituted-β-amino acid bearing an aryl substituent in the α position.

9. A method according to claim 1, wherein the β-amino acid is an α-substituted-β-amino acid bearing an alkoxy substituent in the α position.

10. A method according to claim 1, wherein the α-amino acid is an α-substituted-β-amino acid bearing a halogen atom substituent in the α position.

11. A method according to claim 1, wherein the β-amino acid is an α-substituted-β-amino acid bearing a fluorine atom substituent in the α position.

12. A method according to claim 1, wherein the β-amino acid is an α,α-disubstituted-β-amino acid.

13. A method according to claim 1, wherein the β-amino acid is an β-unsubstituted-β-amino acid.

14. A method according to claim 1, wherein the β-amino acid is an α-substituted-β-unsubstituted-β-amino acid.

15. A method according to claim 1, wherein the β-amino acid is an α-substituted-β-substituted-β-amino acid.

16. A method according to claim 1, wherein the β-amino acid is an α-substituted-β-substituted-β-amino acid bearing an aryl substituent in the β position.

17. A method according to claim 1, wherein the β-amino acid is an α-substituted-β-substituted-β-amino acid bearing an aryl substituent in the α position.

18. A method according to claim 1, wherein the β-amino acid is an α-substituted-β-substituted-β-amino acid bearing an aryl substituent in the α position and an aryl substituent in the β position.

19. A method according to claim 1, wherein the β-amino acid has the following formula:

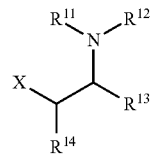

where $R^{11}$ and $R^{12}$ are independently selected from H, an alkyl group, and an aryl group or $R^{11}$ and $R^{12}$, together with the nitrogen atom to which they are bonded, form a ring; where $R^{13}$ is selected from a hydrogen atom, an alkyl group, an aryl group, and a carboxylic acid group other than COOH; where $R^{14}$ is selected from a hydrogen atom, an alkyl group, an aryl group, a hydroxy group, an alkoxy group, other groups having the formula —OP (P representing a hydroxy protecting moiety), a thiol group, an alkylthio group, an arylthio group, an amine group, a carboxylic acid group, a phosphine group, a sulfonic acid group, and a halogen atom; or where $R^{13}$ and $R^{14}$, together with the carbon atoms to which they are bonded, form a ring; and where X is a carboxylic acid group; wherein the chiral 2-substituted-isoxazolidin-5-one has the following formula:

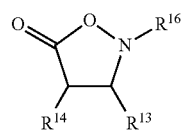

where $R^{16}$ is a substituted or unsubstituted alkyl group or a substituted or unsubstituted aryl group; and wherein the α,β-unsaturated imide has the following formula:

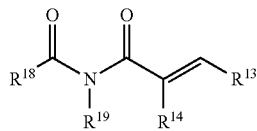

where $R^{18}$ is a substituted or unsubstituted alkyl group, a substituted or unsubstituted aryl group, or an alkoxy group, and where $R^{19}$ is a hydrogen atom, a substituted or unsubstituted alkyl group, or a substituted or unsubstituted aryl group, or where $R^{18}$ and $R^{19}$, together with the atoms to which they are bonded, faun a ring; provided that at least one of the following three conditions is met: (i) $R^{19}$ is a hydrogen atom; (ii) $R^{14}$ is not a hydrogen atom; (iii) $R^{13}$ is a hydrogen atom.

20. A method according to claim 19, wherein $R^{19}$ is a hydrogen atom and where $R^{18}$ is a substituted or unsubstituted alkyl group, a substituted or unsubstituted aryl group, or an alkoxy group.

21. A method according to claim 19, wherein the chiral Lewis acid is a chiral Lewis acid complex.

22. A method according to claim 19, wherein said converting the 2-substituted-isoxazolidin-5-one to the β-amino acid is carried out by hydrogenation.

23. A method according to claim 22, wherein said chiral Lewis acid comprises a chiral Lewis acid complex.

24. A method according to claim 19, wherein $R^{14}$ is not hydrogen.

25. A method according to claim 19, wherein $R^{14}$ is an alkyl group.

26. A method according to claim 19, wherein $R^{14}$ is an aryl group.

27. A method according to claim 19, wherein $R^{14}$ is an alkoxy group.

28. A method according to claim 19, wherein $R^{14}$ is a halogen atom.

29. A method according to claim 19, wherein $R^{14}$ is a fluorine atom.

30. A method according to claim 19, wherein $R^{13}$ is hydrogen.

31. A method according to claim 19, wherein $R^{13}$ is hydrogen and wherein $R^{14}$ is not hydrogen.

32. A method according to claim 19, wherein $R^{13}$ is not hydrogen and wherein $R^{14}$ is not hydrogen.

33. A method according to claim 19, wherein $R^{14}$ is not hydrogen and wherein $R^{13}$ is an aryl group.

34. A method according to claim 19, wherein $R^{3}$ is not hydrogen and wherein $R^{14}$ is an aryl group.

35. A method according to claim 19, wherein $R^{13}$ is an aryl group and wherein $R^{14}$ is an aryl group.

36. A method for making a chiral 2-substituted-isoxazolidin-5-one, said method comprising:
providing an α,β-unsaturated imide; and
cyclizing the α,β-unsaturated imide using a chiral Lewis acid and a substituted hydroxyl amine to produce the chiral 2-substituted-isoxazolidin-5-one; provided that at least one of the following three conditions is met: (i) a hydrogen atom is bonded to the α,β-unsaturated imide's imide nitrogen; (ii) the chiral 2-substituted-isoxazolidin-5-one is substituted in the 4 position; (iii) the chiral 2-substituted-isoxazolidin-5-one is unsubstituted in the 3 position.

37. A method according to claim 36, wherein a hydrogen atom is bonded to the α,β-unsaturated imide's imide nitrogen.

38. A method according to claim 36, wherein the Lewis acid is a chiral Lewis acid complex.

39. A method according to claim 36, wherein the chiral 2-substituted-isoxazolidin-5-one is substituted in the 4 position.

40. A method according to claim 36, wherein the chiral 2-substituted-isoxazolidin-5-one is substituted in the 4 position with an alkyl substituent.

41. A method according to claim 36, wherein the chiral 2-substituted-isoxazolidin-5-one is substituted in the 4 position with an aryl substituent.

42. A method according to claim 36, wherein the chiral 2-substituted-isoxazolidin-5-one is substituted in the 4 position with an alkoxy substituent.

43. A method according to claim 36, wherein the chiral 2-substituted-isoxazolidin-5-one is substituted in the 4 position with a halogen atom.

44. A method according to claim 36, wherein the chiral 2-substituted-isoxazolidin-5-one is substituted in the 4 position with a fluorine atom.

45. A method according to claim 36, wherein the chiral 2-substituted-isoxazolidin-5-one is disubstituted in the 4 position.

46. A method according to claim 36, wherein the chiral 2-substituted-isoxazolidin-5-one is unsubstituted in the 3 position.

47. A method according to claim 36, wherein the chiral 2-substituted-isoxazolidin-5-one is substituted in the 4 position and unsubstituted in the 3 position.

48. A method according to claim 36, wherein the chiral 2-substituted-isoxazolidin-5-one is substituted in the 3 position and substituted in the 4 position.

49. A method according to claim 36, wherein the chiral 2-substituted-isoxazolidin-5-one is substituted in the 3 position with an aryl substituent and is substituted in the 4 position.

50. A method according to claim 36, wherein the chiral 2-substituted-isoxazolidin-5-one is substituted in the 4 position with an aryl substituent and is substituted in the 3 position.

51. A method according to claim 36, wherein the chiral 2-substituted-isoxazolidin-5-one is substituted in the 3 position with an aryl substituent and is substituted in the 4 position with an aryl substituent.

* * * * *

UNITED STATES PATENT AND TRADEMARK OFFICE
CERTIFICATE OF CORRECTION

PATENT NO.       : 8,034,974 B2
APPLICATION NO.  : 10/895647
DATED            : October 11, 2011
INVENTOR(S)      : Sibi et al.

It is certified that error appears in the above-identified patent and that said Letters Patent is hereby corrected as shown below:

Column 44, Line 25 (Claim 10)
Delete "α-amino" and insert --β-amino--

Column 45, Line 34 (Claim 19)
Delete "faun" and insert --form--

Column 46, Line 3 (Claim 34)
Delete "$R^3$" and insert --$R^{13}$--

Signed and Sealed this
Sixth Day of December, 2011

David J. Kappos
*Director of the United States Patent and Trademark Office*